US012337291B2

(12) United States Patent
Dabrowski et al.

(10) Patent No.: US 12,337,291 B2
(45) Date of Patent: Jun. 24, 2025

(54) GUIDE RNA SYNTHESIS SYSTEM AND METHOD

(71) Applicant: Synthego Corporation, Redwood City, CA (US)

(72) Inventors: Paul Dabrowski, Atherton, CA (US); Fabian Gerlinghaus, San Francisco, CA (US); Reed Kelso, San Francisco, CA (US); John Andrew Walker, II, San Leandro, CA (US)

(73) Assignee: Synthego Corporation, Redwood City, CA (US)

( * ) Notice: Subject to any disclaimer, the term of this patent is extended or adjusted under 35 U.S.C. 154(b) by 0 days.

(21) Appl. No.: 16/989,593

(22) Filed: Aug. 10, 2020

(65) Prior Publication Data

US 2021/0047668 A1 Feb. 18, 2021

Related U.S. Application Data

(63) Continuation of application No. 16/130,901, filed on Sep. 13, 2018, now abandoned, which is a continuation of application No. PCT/US2018/050306, filed on Sep. 10, 2018.

(60) Provisional application No. 62/556,791, filed on Sep. 11, 2017.

(51) Int. Cl.
| | |
|---|---|
| *C12P 19/34* | (2006.01) |
| *B01J 19/00* | (2006.01) |
| *B01L 7/00* | (2006.01) |
| *C07H 1/00* | (2006.01) |
| *C07K 1/04* | (2006.01) |
| *C12N 15/10* | (2006.01) |
| *C40B 50/14* | (2006.01) |

(52) U.S. Cl.
CPC ............ B01J 19/0046 (2013.01); B01L 7/52 (2013.01); C07H 1/00 (2013.01); C07K 1/045 (2013.01); C07K 1/047 (2013.01); C12N 15/10 (2013.01); C12N 15/1093 (2013.01); C40B 50/14 (2013.01); *B01J 2219/00306* (2013.01); *B01J 2219/00351* (2013.01); *B01J 2219/00418* (2013.01); *B01J 2219/00423* (2013.01); *B01J 2219/00454* (2013.01); *B01J 2219/00495* (2013.01); *B01J 2219/00596* (2013.01); *B01J 2219/00695* (2013.01); *B01J 2219/00722* (2013.01); *B01J 2219/00725* (2013.01)

(58) Field of Classification Search
CPC ........ C40B 50/14; C07H 1/00; B01J 19/0046; C12N 15/1093
USPC ......................................... 535/126; 536/25.3
See application file for complete search history.

(56) References Cited

U.S. PATENT DOCUMENTS

| | | | |
|---|---|---|---|
| 4,517,338 A | 5/1985 | Urdea et al. | |
| 4,598,049 A | 7/1986 | Zelinka et al. | |
| 5,175,209 A | 12/1992 | Beattie et al. | |
| 5,368,823 A | 11/1994 | Mcgraw et al. | |
| 5,429,807 A | 7/1995 | Matson et al. | |
| 5,447,692 A | 9/1995 | Keenan et al. | |
| 5,472,672 A | 12/1995 | Brennan | |
| 5,474,796 A | 12/1995 | Brennan | |
| 5,529,756 A | 6/1996 | Brennan | |
| 5,554,501 A | 9/1996 | Coassin et al. | |
| 5,604,097 A | 2/1997 | Brenner | |
| 5,614,608 A | 3/1997 | Krchnak et al. | |
| 5,643,738 A | 7/1997 | Zanzucchi et al. | |
| 5,681,534 A | 10/1997 | Neves | |
| 5,716,584 A | 2/1998 | Baker et al. | |
| 5,750,341 A | 5/1998 | Macevicz | |
| 5,750,672 A | 5/1998 | Kempe | |
| 5,766,556 A | 6/1998 | Dewitt et al. | |
| 5,770,157 A | 6/1998 | Cargill et al. | |
| 5,814,700 A | 9/1998 | Brennan | |
| 5,846,719 A | 12/1998 | Brenner et al. | |
| 5,865,224 A | 2/1999 | Ally et al. | |
| 5,888,830 A | 3/1999 | Mohan et al. | |
| 5,969,119 A | 10/1999 | Macevicz | |
| 5,981,733 A | 11/1999 | Gamble et al. | |
| 6,001,311 A | 12/1999 | Brennan | |
| 6,013,445 A | 1/2000 | Albrecht et al. | |
| 6,022,963 A | 2/2000 | Mcgall et al. | |
| 6,024,925 A | 2/2000 | Little et al. | |
| 6,033,631 A | 3/2000 | Zuckermann et al. | |
| 6,040,193 A | 3/2000 | Winkler et al. | |
| 6,042,789 A | 3/2000 | Antonenko et al. | |
| 6,045,755 A | 4/2000 | Lebl et al. | |
| 6,051,439 A | 4/2000 | Antonenko et al. | |
| 6,054,325 A | 4/2000 | Kedar et al. | |
| 6,069,243 A | 5/2000 | Scozzari | |
| 6,080,318 A | 6/2000 | Gumm et al. | |

(Continued)

FOREIGN PATENT DOCUMENTS

| | | |
|---|---|---|
| EP | 0688008 A1 | 12/1995 |
| EP | 1119578 B1 | 6/2004 |

(Continued)

OTHER PUBLICATIONS

Dellinger et al. (JACS, 2011, 133, 11540-11556). (Year: 2011).*

(Continued)

*Primary Examiner* — Amy M Bunker
(74) *Attorney, Agent, or Firm* — Quarles & Brady, LLP

(57) ABSTRACT

The present invention provides improved automated systems and methods for synthesis of biopolymers including DNA and RNA. The automated systems and methods represent a number of improvements over existing systems for multiplex synthesis of biopolymers in a combinatorial fashion.

15 Claims, 9 Drawing Sheets

Specification includes a Sequence Listing.

(56) References Cited

U.S. PATENT DOCUMENTS

| | | |
|---|---|---|
| 6,083,682 A | 7/2000 | Campbell et al. |
| 6,117,397 A | 9/2000 | Antonenko et al. |
| 6,121,054 A | 9/2000 | Lebl |
| 6,126,904 A | 10/2000 | Zuellig et al. |
| 6,143,252 A | 11/2000 | Haxo, Jr. et al. |
| 6,149,869 A | 11/2000 | Antonenko et al. |
| 6,168,914 B1 | 1/2001 | Campbell et al. |
| 6,171,797 B1 | 1/2001 | Perbost |
| 6,267,930 B1 | 7/2001 | Ruediger et al. |
| 6,270,730 B1 | 8/2001 | McLuen et al. |
| 6,274,091 B1 | 8/2001 | Mohan et al. |
| 6,306,597 B1 | 10/2001 | Macevicz |
| 6,329,210 B1 | 12/2001 | Schleifer |
| 6,346,423 B1 | 2/2002 | Schembri |
| 6,518,067 B1 | 2/2003 | Frank et al. |
| 6,532,978 B1 | 3/2003 | Mueller-Kuhrt et al. |
| 6,663,832 B2 | 12/2003 | Lebl et al. |
| 6,693,187 B1 | 2/2004 | Dellinger et al. |
| 6,768,005 B2 | 7/2004 | Mellor et al. |
| 6,811,755 B2 | 11/2004 | McLuen et al. |
| 6,846,454 B2 | 1/2005 | Peck |
| 6,867,050 B2 | 3/2005 | Peck et al. |
| 6,887,715 B2 | 5/2005 | Schembri |
| 6,911,151 B1 | 6/2005 | Mueller-Kuhrt et al. |
| 6,932,943 B1 | 8/2005 | Cracauer et al. |
| 7,067,641 B2 | 6/2006 | Dellinger et al. |
| 7,115,400 B1 | 10/2006 | Adessi et al. |
| 7,150,998 B2 | 12/2006 | McLuen et al. |
| 7,192,558 B2 | 3/2007 | McLuen et al. |
| 7,249,529 B2 | 7/2007 | Massaro |
| 7,273,933 B1 | 9/2007 | Krotz et al. |
| 7,321,828 B2 | 1/2008 | Cowsert et al. |
| 7,378,259 B2 | 5/2008 | Bahatt et al. |
| 7,390,459 B2 | 6/2008 | Lebl et al. |
| 7,411,061 B2 | 8/2008 | Myerson et al. |
| 7,413,714 B1 | 8/2008 | Schwalbe et al. |
| 7,435,390 B2 | 10/2008 | Cracauer et al. |
| 7,435,392 B2 | 10/2008 | Oberbeck et al. |
| 7,576,037 B2 | 8/2009 | Engelhardt et al. |
| 7,604,996 B1 | 10/2009 | Stuelpnagel et al. |
| 7,647,186 B2 | 1/2010 | Fowler et al. |
| 7,745,591 B2 | 6/2010 | Dellinger et al. |
| 7,858,364 B2 | 12/2010 | Brennan |
| 7,914,739 B2 | 3/2011 | Heiner et al. |
| 8,073,666 B2 | 12/2011 | Fowler et al. |
| 8,084,245 B2 | 12/2011 | Brennan |
| RE43,097 E | 1/2012 | Albrecht et al. |
| 8,147,776 B2 | 4/2012 | McLuen et al. |
| 8,158,085 B2 | 4/2012 | McLuen et al. |
| 8,198,028 B2 | 6/2012 | Rigatti et al. |
| 8,211,370 B2 | 7/2012 | Downing |
| 8,404,196 B2 | 3/2013 | McLuen et al. |
| 8,415,138 B2 | 4/2013 | Leproust |
| 8,450,107 B1 | 5/2013 | Zhang et al. |
| 8,465,694 B2 | 6/2013 | Lebl et al. |
| 8,481,309 B2 | 7/2013 | Zhang et al. |
| 8,507,272 B2 | 8/2013 | Zhang et al. |
| 8,575,071 B2 | 11/2013 | Lau et al. |
| 8,586,728 B2 | 11/2013 | Sproat |
| 8,614,092 B2 | 12/2013 | Zhang et al. |
| 8,642,354 B2 | 2/2014 | Ermakov et al. |
| 8,652,810 B2 | 2/2014 | Adessi et al. |
| 8,669,053 B2 | 3/2014 | Stuelpnagel et al. |
| 8,697,359 B1 | 4/2014 | Zhang |
| 8,731,721 B2 | 5/2014 | Heiner et al. |
| 8,747,780 B2 | 6/2014 | McLuen et al. |
| 8,771,945 B1 | 7/2014 | Zhang |
| 8,784,745 B2 | 7/2014 | Nelson et al. |
| 8,795,965 B2 | 8/2014 | Zhang |
| 8,808,986 B2 | 8/2014 | Jacobson et al. |
| 8,846,898 B2 | 9/2014 | Dellinger et al. |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,040,678 B2 | 5/2015 | Steemers et al. |
| 9,069,358 B2 | 6/2015 | Demmitt |
| 9,073,033 B2 | 7/2015 | Lebl et al. |
| 9,079,148 B2 | 7/2015 | Rigatti et al. |
| 9,115,348 B2 | 8/2015 | Haurwitz et al. |
| 9,150,896 B2 | 10/2015 | Chen et al. |
| 9,238,671 B2 | 1/2016 | Goryshin et al. |
| 9,283,535 B2 | 3/2016 | Butler et al. |
| 9,297,006 B2 | 3/2016 | Adessi et al. |
| 9,322,063 B2 | 4/2016 | Zhao |
| 9,370,551 B2 | 6/2016 | Cong et al. |
| 9,416,411 B2 | 8/2016 | Stuelpnagel et al. |
| 9,492,820 B2 | 11/2016 | Reed et al. |
| 9,506,055 B2 | 11/2016 | Lau et al. |
| 9,598,453 B2 | 3/2017 | Steemers et al. |
| 9,677,069 B2 | 6/2017 | Rigatti et al. |
| 9,745,573 B2 | 8/2017 | Stuelpnagel et al. |
| 9,765,396 B2 | 9/2017 | Zhao et al. |
| 9,856,471 B2 | 1/2018 | Jacobson et al. |
| 9,981,239 B2 | 5/2018 | Banyai et al. |
| 10,040,048 B1 | 8/2018 | Dabrowski et al. |
| 10,569,249 B2 | 2/2020 | Dabrowski et al. |
| 10,744,477 B2 | 8/2020 | Banyai et al. |
| 10,814,300 B2 | 10/2020 | Dabrowski et al. |
| 10,851,367 B2 * | 12/2020 | Liras ............... A61K 47/549 |
| 2001/0028866 A1 | 10/2001 | Ecker et al. |
| 2001/0051114 A1 | 12/2001 | McLuen et al. |
| 2002/0028159 A1 | 3/2002 | Lebl et al. |
| 2002/0031833 A1 | 3/2002 | Heyneker et al. |
| 2002/0044894 A1 | 4/2002 | Lebl et al. |
| 2002/0048536 A1 | 4/2002 | Bergh et al. |
| 2002/0123133 A1 | 9/2002 | Mehta et al. |
| 2002/0142341 A1 | 10/2002 | Kameyama et al. |
| 2002/0142454 A1 | 10/2002 | Cracauer et al. |
| 2002/0176811 A1 | 11/2002 | Peck et al. |
| 2003/0069411 A1 | 4/2003 | Brennan |
| 2003/0072689 A1 | 4/2003 | Cracauer et al. |
| 2003/0086829 A1 | 5/2003 | Livesay et al. |
| 2003/0113237 A1 | 6/2003 | Cracauer et al. |
| 2003/0118717 A1 | 6/2003 | Peck |
| 2003/0182068 A1 | 9/2003 | Battersby et al. |
| 2003/0223909 A1 | 12/2003 | Oberbeck et al. |
| 2004/0132040 A1 | 7/2004 | Hamill |
| 2004/0151628 A1 | 8/2004 | Honkanen et al. |
| 2004/0223885 A1 | 11/2004 | Keen et al. |
| 2004/0241998 A1 | 12/2004 | Hanson |
| 2005/0169816 A1 | 8/2005 | Kirshner |
| 2005/0244885 A1 | 11/2005 | Wolber et al. |
| 2005/0281719 A1 | 12/2005 | Brennan |
| 2006/0019264 A1 | 1/2006 | Attiya et al. |
| 2006/0182609 A1 | 8/2006 | Guerra |
| 2007/0096674 A1 | 5/2007 | Hashimoto et al. |
| 2007/0110638 A1 | 5/2007 | Heiner et al. |
| 2007/0117109 A1 | 5/2007 | Rothemund |
| 2007/0117178 A1 | 5/2007 | Heiner et al. |
| 2007/0128084 A1 | 6/2007 | Coassin et al. |
| 2007/0184546 A1 | 8/2007 | Farrelly et al. |
| 2007/0276965 A1 | 11/2007 | Johnson et al. |
| 2008/0026096 A1 | 1/2008 | Rozema et al. |
| 2008/0038724 A9 | 2/2008 | Behlke et al. |
| 2008/0058511 A1 | 3/2008 | Hargreaves et al. |
| 2008/0058512 A1 | 3/2008 | Leproust |
| 2008/0261220 A1 | 10/2008 | Cracauer et al. |
| 2009/0023605 A1 | 1/2009 | Lebl et al. |
| 2009/0041634 A1 | 2/2009 | Cracauer et al. |
| 2009/0054605 A1 | 2/2009 | Brennan |
| 2009/0148353 A1 | 6/2009 | Downing |
| 2010/0248981 A1 | 9/2010 | Shirazi |
| 2010/0273264 A1 | 10/2010 | Stout et al. |
| 2011/0021749 A1 | 1/2011 | Demmitt |
| 2011/0028340 A1 | 2/2011 | Hamill |
| 2011/0123411 A1 | 5/2011 | Butler |
| 2011/0124529 A1 | 5/2011 | Brennan |

(56) References Cited

U.S. PATENT DOCUMENTS

| | | | |
|---|---|---|---|
| 2011/0136696 A1 | 6/2011 | Heiner et al. | |
| 2011/0143965 A1 | 6/2011 | Lebl et al. | |
| 2011/0172127 A1 | 7/2011 | Jacobson et al. | |
| 2011/0177514 A1 | 7/2011 | Froehlich et al. | |
| 2012/0022966 A1 | 1/2012 | Raab et al. | |
| 2012/0141797 A1* | 6/2012 | Sherman | B82Y 30/00 |
| | | | 428/403 |
| 2012/0220497 A1 | 8/2012 | Jacobson et al. | |
| 2012/0308346 A1 | 12/2012 | Keigler et al. | |
| 2013/0165349 A1 | 6/2013 | Butler et al. | |
| 2013/0296192 A1 | 11/2013 | Jacobson et al. | |
| 2014/0273037 A1 | 9/2014 | Wu | |
| 2014/0273233 A1 | 9/2014 | Chen et al. | |
| 2014/0274809 A1 | 9/2014 | Harvey et al. | |
| 2014/0309119 A1 | 10/2014 | Jacobson et al. | |
| 2014/0357530 A1 | 12/2014 | Zhang et al. | |
| 2015/0038373 A1 | 2/2015 | Banyai et al. | |
| 2015/0071889 A1 | 3/2015 | Musunuru et al. | |
| 2015/0369267 A1 | 12/2015 | Bailey et al. | |
| 2016/0068864 A1* | 3/2016 | Doudna | C12N 15/111 |
| | | | 435/188 |
| 2016/0177304 A1* | 6/2016 | Collingwood | C12N 15/111 |
| | | | 536/24.1 |
| 2016/0194629 A1 | 7/2016 | Hinz et al. | |
| 2016/0256844 A1 | 9/2016 | Butler | |
| 2017/0204407 A1* | 7/2017 | Gilbert | C12N 15/1082 |
| 2017/0355985 A1* | 12/2017 | Dellinger | C12N 15/11 |
| 2018/0194795 A1 | 7/2018 | Hennecke et al. | |
| 2018/0237818 A1 | 8/2018 | Sampson et al. | |
| 2018/0264428 A1 | 9/2018 | Banyai et al. | |
| 2019/0076814 A1 | 3/2019 | Dabrowski et al. | |
| 2019/0366293 A1 | 12/2019 | Banyai et al. | |

FOREIGN PATENT DOCUMENTS

| | | |
|---|---|---|
| EP | 2332896 A2 | 6/2011 |
| EP | 2331558 B1 | 9/2018 |
| JP | 2018513682 A | 5/2018 |
| JP | 2018527311 A | 9/2018 |
| WO | WO-9002605 A1 | 3/1990 |
| WO | WO-9833586 A1 | 8/1998 |
| WO | WO-0056445 A1 | 9/2000 |
| WO | WO-2004029223 A2 | 4/2004 |
| WO | WO-2006044956 A1 | 4/2006 |
| WO | WO-2014131833 A1 | 9/2014 |
| WO | WO-2018126176 A1 | 7/2018 |
| WO | WO-2018201086 A1 | 11/2018 |
| WO | WO-2019051430 A1 | 3/2019 |
| WO | WO-2020009700 A1 | 1/2020 |

OTHER PUBLICATIONS

Dellinger et al., Streamlined Process for the Chemical Synthesis of RNA Using 2'-O-thionocarbamate-protected Nucleoside Phosphoramidites in the Solid Phase, Journal of the American Chemical Society, 2011, 133, 11540-11556. (Year: 2011).*
Houghten, R., General Method for the Rapid Solid-Phase Synthesis of Large Nos. of Peptides: Specificity of Antigen-Antibody Interaction at the Level of Individual Amino Acids, Proc. Natl. Acad. Sci., 1985, 82, 5131-5135. (Year: 1985).*
Dellinger et al., Streamlined Process for the Chemical Synthesis of RNA Using 2'-O-Thionocarbamate-Protected Nucleoside Phosphoramidites in the Solid Phase, Journal of American Chemical Society, 2011, 133, 11540-11556. (Year: 2011).*
Advanced Analytical®, Oligo Pro™ Automated Purity Analyzers, 2016, 4 pages.
Applied Biosystems, Applied Biosystems 3400 DNA Synthesizer, © 2007, 4 pages.
Asahi Kasei Bioprocess, Oligonucleotide Synthesizers,© 2014 Asahi Kasei Bioprocess—All rights reserved, 4 pages.
Beckman Instruments Inc., Oligo Series 1000 DNA Synthesis Systems, BR-8046A, © 1996 Beckman Instruments Inc., 12 Pages.
CTc Analytics, HPLC Pal Systems, Front-End Automation for LC/LC-MS Systems, © 2017, 8 pages.
Dr.Oligo®, AZCO BioTech, Inc.,—96/192 DNA/RNA High throughput Synthesizer, 2014, 24 pages.
General Electric Company © 2006, AKTA oligopilot plus, Oligonucleotide synthesis, Data File 18-1144-66 AD, Mar. 2006, 8 pages.
J. Karafilidis, Oligonucleotide Synthesis. Acros Organics Part of Thermo Fisher Scientific, 2008, 8 pages.
Jensen et al., Next generation 1536-well oligonucleotide synthesizer with on-the-fly dispense. Journal of Biotechnology 171 (2014) 76-81.
Kosuri and Church, "Large-scale de novo DNA synthesis: technologies and applications," Nature Methods, 11:499-507, 2014. Available at: http://www.nature.com/nmeth/journal/v11/n5/full/nmeth.2918.html.
Lashkari, et al. An automated multiplex oligonucleotide synthesizer: development of high-throughput, low-cost DNA synthesis. Proc Natl Acad Sci U S A. Aug. 15, 1995;92(17):7912-5.
Linda E Sindelar et al, High-throughput DNA synthesis in a multichannel format. Nucleic Acids Research,23.6 ( 1995): 982-987, © 1995 Oxford University Press.
Marco Karsten et al., Increasing Throughput in LC and LC-MS with a Parallel HPLC System, PITTCON 2006 Presentation, Dionex Corporation, © 2006, 5 pages.
PCT/US2018/040906 International Search Report and Written Opinion dated Oct. 29, 2018.
PCT/US2018/050306 International Search Report and Written Opinion dated Dec. 24, 2018.
Richard C King et al, Description and validation of a staggered parallel high performance liquid chromatography system for good laboratory practice level quantitative analysis by liquid chromatography/tandem mass spectrometry. Rapid Commun_ Mass Spectrum_ 2002; 16: 43-52, Copyright © 2001 John Wiley & Sons, Ltd.
Sepiatec GmbH, Technical Data Sepmatix 8x HPLC, © copyright 2012 Sepiatec GmbH, 4 pages.
Teledyne Isco, A Teledyne Technologies Company, CombiFlash® Optix 10 Installation and Operation Guide, Copyright © 2000, Teledyne Isco, Inc., Revision F, May 1, 2007, 82 pages.
Thermo Fisher Scientific Inc., Multiplexing Technology Thermo Scientific Transcend LX System, Product Specifications, © 2010, 2 Pages.
U.S. Appl. No. 14/866,091 Notice of Allowance dated May 9, 2018.
U.S. Appl. No. 16/027,982 Notice of Allowance dated Oct. 21, 2019.
U.S. Appl. No. 16/027,982 Office Action dated Jun. 27, 2019.
U.S. Appl. No. 14/866,091 Non Final Office Action dated Dec. 18, 2017.
U.S. Appl. No. 16/027,982 Notice of Allowance dated Nov. 27, 2019.
U.S. Appl. No. 16/746,729 Notice of Allowance dated Jul. 8, 2020.
U.S. Appl. No. 16/746,729 Office Action dated Mar. 9, 2020.
Waters the Science of What's Possible™, Alliance HPLC High Through System, © Oct. 2008, 7 pages.
Cheng, et al. High throughput parallel synthesis of oligonucleotides with 1536 channel synthesizer. Nucleic Acids Res. 30(18):e93, 2002.
Coin et al. Solid-phase peptide synthesis: from standard procedures to the synthesis of difficult sequences. Nature Protocols 2(12):3247-3256 (Dec. 13, 2007). doi: 10.1038/nprot.2007.454.
Co-pending U.S. Appl. No. 17/021,616, inventors Dabrowski; Paul et al., filed on Sep. 15, 2020.
GB2004065.5 Office Action dated Aug. 10, 2020.
Simon Rayner et al., MerMade: An Oligodeoxyribonucleotide Synthesizer for High Throughput Oligonucleotide Production in Duai96-Well Plates. Genome Research, 8:741-747 © 1998 by Cold Spring Harbor Laboratory Press ISSN 1054-9803/98, 7 Pages.
Solid-Phase Oligonucleotide Synthesis. Part of the Nucleic Acids Book (http://www.atdbio.com/nucleic-acids-book). Copyright ATDBio Ltd. 2005-2018. 18 pages. Retrieved May 1, 2018 at URL: http://www.atdbio.com/nucleic-acids-book.
U.S. Appl. No. 16/130,901 Office Action dated Aug. 14, 2020.
U.S. Appl. No. 16/130,901 Office Action dated Jun. 10, 2020.

(56) References Cited

OTHER PUBLICATIONS

U.S. Appl. No. 16/746,729 Notice of Allowance dated Aug. 28, 2020.
Briner et al. Guide RNA functional modules direct Cas9 activity and orthogonality. Mol Cell 56(2):333-339 (2014).
EP18853902.7 Extended European Search Report dated May 4, 2021.
GB2004065.5 Office Action dated Feb. 26, 2021.
PCT/US2018/040906 International Preliminary Report on Patentability dated Jan. 5, 2021.
PCT/US2018/050306 International Preliminary Report on Patentability dated Mar. 17, 2020.

* cited by examiner

SEQUENCE LISTING

```
<160> NUMBER OF SEQ ID NOS: 3

<210> SEQ ID NO 1
<211> LENGTH: 16
<212> TYPE: PRT
<213> ORGANISM: Drosophila sp.

<400> SEQUENCE: 1

Arg Gln Ile Lys Ile Trp Phe Gln Asn Arg Arg Met Lys Trp Lys Lys
1               5                   10                  15

<210> SEQ ID NO 2
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
uuacuucuga caacgaucgg uuacuucuga caacgaucgg uuacuucuga caacgaucgg      60
uuacuucuga caacgaucgg                                                  80

<210> SEQ ID NO 3
<211> LENGTH: 103
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 3
cuaagccgac aguucugcag cauuuacuuc ugacaacgau cgguuacuuc ugacaacgau      60
cgguuacuuc ugacaacgau cgguuacuuc ugacaacgau cgg                       103
```

GUIDE RNA SYNTHESIS SYSTEM AND METHOD

CROSS REFERENCE

This application is a continuation of U.S. patent application Ser. No. 16/130,901, filed Sep. 13, 2018, which is a continuation of PCT Application No. PCT/US2018/050306, filed Sep. 10, 2018, which claims the benefit of U.S. Provisional Application No. 62/556,791, filed Sep. 11, 2017, all of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Oct. 1, 2020, is named 1000-302_SL.txt and is 1,120 bytes in size.

BACKGROUND OF THE INVENTION

Polymer synthesis (e.g. DNA and RNA synthesis) requires a complex sequence of synthesis steps. Chemical synthesis of polymers such as DNA and RNA is typically performed on solid support medium (SSM), wherein a series of repetitive steps deblock and couple (and in the case of oligonucleotides, also oxidize and cap) the growing polymer chain attached to the SSM. Single channel automated synthesis systems (e.g. oligosynthesizers) are available which automate the steps of the polymer synthesis cycle described above. Multi-channel synthesizers for the simultaneous synthesis of multiple different polymers (e.g. multiple different DNA or RNA oligonucleotide sequences) are also available. In general such systems utilize open microplates to provide multiple vessels in which polymers are synthesized. A delivery head under computer control moves over the reaction plate to deliver the required reagents to each vessel sequentially. Different activated monomer (e.g. phosphoramidite) reagents may be delivered to different vessels. After the required activated monomer (e.g. phosphoramidite) reagents have been delivered to all of reaction vessels, suction is applied to all of the reaction vessels at the same time to draw the reagent through the SSM reaction media. Upon completion of the synthesis, the polymer chain of desired length is cleaved from its chemical attachment to the SSM reaction medium

SUMMARY OF THE INVENTION

The present invention relates to systems and methods for biopolymer synthesis. In particular embodiments, the present invention relates to systems and methods for synthesis of DNA, RNA, and peptides. Although the synthesis systems and methods described herein are particularly applicable to the synthesis of DNA and RNA, the systems and method may be readily adapted by substitution or addition of various reagents to the synthesis of a wide range of organic polymers or biopolymers where it is necessary or desirable to synthesize a large number of different compounds in an automated and efficient manner.

DNA and RNA synthesis, for example, requires a complex sequence of synthesis steps. Chemical synthesis of DNA and RNA is typically performed on solid support medium (SSM) such as polystyrene beads or controlled pore glass (CPG). The SSM is chemically treated (derivatized) to feature a very large number of accessible free hydroxyl groups which are employed as a collective solid support for oligonucleotide synthesis. In an initial step in the synthesis of an oligonucleotide, the first 3' nucleotide is added to the SSM by reacting the corresponding phosphoramidite with a free hydroxyl group extending from the solid support. Reaction of the phosphoramidite and the free hydroxyl group of the solid support produces single monomer covalently bound per site on the SSM. This single-monomer then serves as the starting point for subsequent monomer-addition cycles. Nucleotide monomers are then added sequentially to the oligonucleotides already covalently bonded to the solid support during monomer-addition cycles. In any particular reaction chamber, a very large number of individual oligonucleotides of a particular sequence are produced dependent upon the order in which phosphoramidite reagents are provided to the chamber.

A monomer-addition cycle is performed for each sequential addition of a monomer to the oligonucleotides already bound to the solid support. The monomer-addition cycle comprises four basic steps. In a deblocking step a blocking group is removed from the 5' hydroxyl of the last-added nucleotide to produce an oligonucleotide with a free 5' hydroxyl group. Then, in the chain elongation step, a next appropriate phosphoramidite is added to the free 5' hydroxyl group, resulting in the nascent oligonucleotide growing by one nucleotide subunit at the 5' end. In the oxidation step, the phosphite link is oxidized to produce a phosphate linkage. In a final step of the monomer-addition cycle, capping agents are added to render any unreacted substrate hydroxyls or unreacted 5' hydroxyls of nascent oligonucleotides unreactive towards subsequent phosphoramidite additions. Sequential repetition of these four steps using the selected phosphoramidite reagents allows the desired oligonucleotide sequence to be synthesized. When a final, desired oligonucleotide with n nucleotide subunits has been synthesized by n−1 iterations of the monomer-addition cycle, the completed oligonucleotide is cleaved from the solid support medium by (for example) addition of a weak acid to generate the final oligonucleotide product in solution.

In each chain elongation step of the monomer addition cycle a small fraction of the available 5' hydroxyl group reactive sites on the oligonucleotides fail to react with the phosphoramidite reagent. These oligonucleotides are capped in the capping step such that they are unreactive in subsequent chain elongation steps. After n−1 iterations of the monomer addition cycle, the result is a mixture of the desired oligonucleotide n nucleotides in length with various truncated oligonucleotides less than n nucleotides in length—these oligonucleotides having failed to react in some chain elongation step and having been capped. The full length oligonucleotides can be separated from the truncated oligonucleotides in a purification step using high pressure liquid phase chromatography.

Peptide synthesis is similar, except that it does not require the capping and oxidation steps. Like oligonucleotide synthesis, it occurs counter to the in vivo direction of synthesis (in this case, C-terminus to N-terminus, rather than the reverse). Like oligonucleotide synthesis, it can be performed on beads with similar chemical properties. It begins with an initial amino-protected (typically Fmoc or Boc group protected) amino acid attached via its carboxyl terminus to the resin via an amide linkage (the resin may be supplied with the amino acid already attached, or it may be supplied as an amino derivatized resin to which the carboxyl terminus of an amino acid can be coupled). The amino group is deprotected to liberate a free nucleophilic amine group. Next, the amine group of the first amino acid is reacted with a second protected amino acid in the presence of a coupling reagent (a carbodiimide, an aminium/uronium salt, or a phosphonium salt, optionally in combination with DIEA). The support is then washed to remove excess reagent, and the deprotection/coupling steps are repeated with the next amino acid. After the addition of the N-terminal most amino acid, the last amino acid is deprotected and the peptide is cleaved from the resin.

Single channel automated synthesis systems (e.g. oligosynthesizers) are available which automate the four steps of the monomer addition cycle described above. The single channel synthesizers add reagents to a single column of SSM in a closed system and perform the four steps for stepwise addition of activated monomers (e.g. phosphoramidite nucleotides) under computer control to generate polymers (e.g. oligonucleotides) having a desired sequence. In contrast, multi-channel synthesizers for the simultaneous synthesis of multiple different polymers (e.g. DNA or RNA sequences) utilize open microplates to provide multiple vessels in which polymers are synthesized, wherein a delivery head under computer control moves over the reaction plate to deliver the required reagents to each vessel sequentially.

Present multi-channel synthesizer (e.g. oligosynthesizer) systems and methods suffer from a number of disadvantages. Because there is only a single delivery head for each reagent (e.g. phosphoramidite), the head must deliver reagent sequentially to each of the reaction vessel which requires the reagent. The reagent delivery takes time which increases with the number of vessels. The time delay for reagent delivery reduces the throughput of the system. The time delay for reagent delivery also increases process variability because the phosphoramidite reagent dwells in the reaction vessels for significantly different periods of time depending upon whether the reagent is delivered early or late in the reagent delivery cycle. Additionally, each reagent requires a separate delivery system. Increasing the number of reagents increases the complexity and cost of the delivery head and also increases the time necessary for delivering reagents. Consequently, the number of different reagents that can be used simultaneously in current synthesis systems is limited. This limits the flexibility of synthesis using for example—modified and/or labeled monomer reagents.

Present multiplex synthesis systems and methods also typically perform reactions in microplates which are exposed to the environment. The open environment allows for introduction of contaminants and reduces the ability of the system to maintain uniformity of reaction parameters such as time of reagent exposure, temperature and mixing. In order to attempt to overcome these limitations and to achieve maximum reaction with available reaction sites, conventional systems and methods utilize a significant excess of reaction time and reagent.
This is wasteful both with respect to the use of expensive reagents and with respect to the increased time need to synthesize oligonucleotides.

Accordingly, there is need for an automated multi-channel synthesis systems and methods which overcome the disadvantages of current systems by increasing system throughput, and synthesis/reagent flexibility while reducing process variability and cycle time thereby allowing synthesis of DNA, RNA, peptides, and other polymer products more quickly and efficiently, with better quality control and reduced waste.

Described herein are automated systems and methods for production of polymers which improve polymer throughput and yield. The automated systems and methods herein can be utilized for synthesis of polymers (e.g. biopolymers) amenable to solid phase synthesis including DNA, RNA, modified nucleic acids, aptamers, peptides, and oligosaccharides. The systems and methods herein can also be used in the synthesis of other non-biological small molecules composed of repeated monomer units. In some embodiments, the system and method automates the synthesis process for peptides while overcoming disadvantages of current systems by increasing system throughput, and synthesis/reagent flexibility while and reducing process variability and cycle time thereby allowing synthesis of DNA/RNA products more quickly and efficiently, with better quality control and reduced waste.

In a particular embodiment the present disclosure describes a multi-stage oligonucleotide synthesis method comprising: synthesis of oligonucleotides bound to solid support medium (SSM) in a first oligosynthesizer; physical transfer of SSM and covalently bound oligonucleotides from the first oligosynthesizer to a second oligosynthesizer; continued synthesis of oligonucleotide sequences at the end of the previously synthesized oligonucleotides in the second oligosynthesizer. The method can include one or more transfer steps, two or more synthesis stages and utilize two or more oligosynthesizers.

In another particular embodiment the present disclosure describes a keyed multi-vessel reaction plate comprising: a body made from a thermally conductive material; one hundred or more reaction vessels in the form of lumens which pass from a first sealing surface of the body to a second sealing surface of the body; and a registration feature configured to engage an oligosynthesizer to ensure correct orientation of keyed multi-vessel reaction plate.

In another particular embodiment the present disclosure describes an oligosynthesizer system and method for controlling temperature of multi-channel reaction plate during oligonucleotide synthesis. The system and method allows for heating the multiple channels of the multi-reaction plate to a selectable temperature. Such temperature control allows for improved reaction kinetics, and uniformity between reaction vessels and monomer addition cycles. Temperature control allows for a reduction in the time taken for each monomer addition step thereby reducing total time for synthesizing a desired oligonucleotide and improving oligosynthesizer throughput.

Thus, the present invention provides improved oligosynthesizer systems and methods. Although the particular synthesis system described in the detailed description below is directed to the synthesis of DNA and RNA, the system and method may be readily adapted by substitution of different reagents to the production of other biopolymers where it is necessary or desirable to produce a large number of different compounds in an automated and efficient manner. Other objects, features and advantages of the invention will be apparent from the drawings and detailed description.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
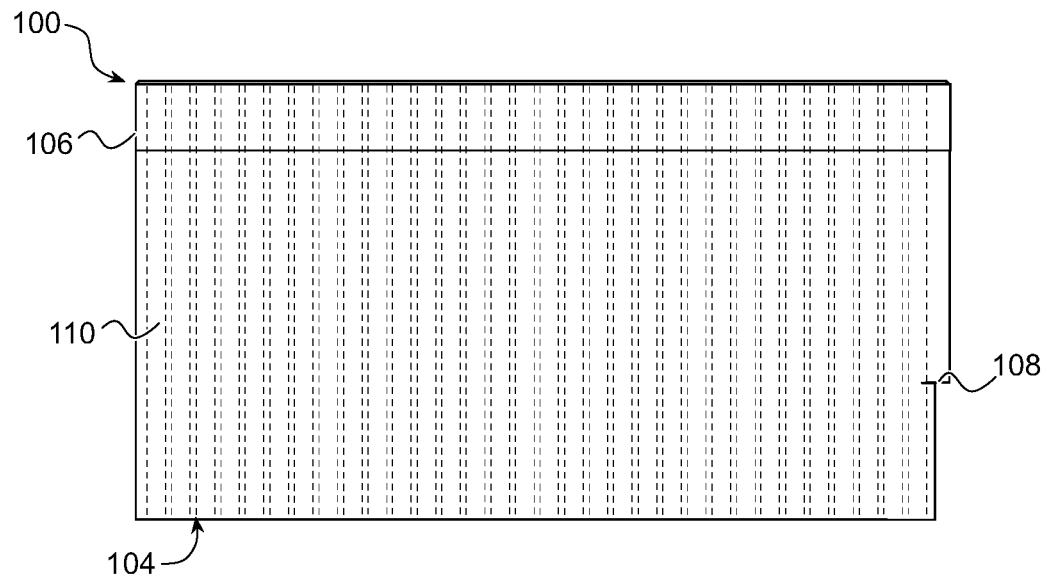
FIGS. 1A, 1B, and 1C show side, top, and bottom views of a reaction plate for synthesizing oligonucleotides according to an embodiment of the present invention.

The following non-limiting embodiments provide illustrative examples of the invention, but do not limit the scope of the invention. Each and all the features described in the present invention are meant to be each and all combinable with each other, irrespective of the claims structure and dependencies. The person skilled in the art will directly and unambiguously derive that singling out particular embodiments of the synthesizer, systems and methods described herein, and combining them with particular other embodiments also described herein, is all part of the present invention.

Embodiment 1. A multiplex biopolymer synthesizer comprising a reagent supply system, a multi-vessel reaction plate, and a reagent control system, wherein the reagent supply system, the multi-vessel reaction plate, and the reagent control system form a closed system during biopolymer elongation.

Embodiment 2. The synthesizer of embodiment 1, wherein the reagent supply system is pressurized and the reagent control system comprises a vacuum system and/or pressurized gas.

Embodiment 3. A computer-controlled system for performing a plurality of different reactions in parallel, each in a separate reaction vessel, wherein the system is configured to be in a closed configuration when one or more reagents are initially delivered to the reaction vessel.

Embodiment 4. The system of embodiment 3, wherein the system is configured to prevent a first reagent of the one or more reagents from contact with moisture from the external environment prior to expulsion of the reagent from the system.

Embodiment 5. The system of embodiment 3 or embodiment 4, wherein one or more reagents comprises a plurality of reagents, and wherein the system is configured to prevent each of the plurality of reagents from contact with moisture from an external environment prior to expulsion of the reagent from the system.

Embodiment 6. The system of any one of embodiments 3-5, wherein the system is configured such that the water content of a first reagent of the one or more reagents never exceeds 10 ppm by weight until at least expulsion of the first reagent from the system.

Embodiment 7. The system of any one of embodiments 3-6, wherein the system is configured to pneumatically:
(a) deliver the first reagent to each of (or a subset of) the reaction vessels;
(b) agitate the first reagent in each of (or a subset of) the reaction vessels to promote mixing within each of the reaction vessels; and
(c) expel the first reagent from each of (or a subset of) the reaction vessels; wherein (a), (b), and (c) occur without the first reagent contacting moisture from an external environment.

Embodiment 8. The system of embodiment 7, wherein the system is configured to pneumatically deliver the first reagent to a subset of the reaction vessels without entering into reaction vessels that are not within the subset.

Embodiment 9. A method for synthesizing a plurality of biopolymers, the method comprising:
obtaining a reaction plate comprising a plurality of reaction vessels, wherein each reaction vessel of the plurality of vessels has a solid phase resin disposed therein;
selectively delivering a first solution from a source that is sealed off from ambient air to a first subset of the plurality of reaction vessels such that the first solution contacts the solid phase resin disposed therein but does not enter into reaction vessels of the plurality of reaction vessels that are not within the first subset; and
ejecting the first solution from the first subset of reaction vessels to an outlet port, wherein the first solution is not exposed to ambient moisture prior to ejection from the outlet port.

Embodiment 10. The method of embodiment 9, further comprising selectively delivering a second solution into a second subset of the plurality of reaction vessels such that the second solution contacts solid phase resin disposed therein, wherein the second subset of the plurality of reactions vessels differs from the first subset of the plurality of reaction vessels.

Embodiment 11. The method of embodiment 9 or embodiment 10, wherein the first solution is simultaneously delivered into each of the reaction vessels of the first subset of the plurality of reaction vessels.

Embodiment 12. The method of any one of embodiments 9-11, wherein each of the plurality of reaction vessels comprises a first porous surface and a second porous surface, wherein the first solution is initially delivered through the first porous surface and ejected through the first porous surface.

Embodiment 13. The method of any one of embodiments 9-12, wherein the first solution comprises a phosphoramidite.

Embodiment 14. The method of any one of embodiments 9-13, further comprising washing the plurality of reactions vessels with a wash fluid (e.g., dry acetonitrile).

Embodiment 15. The method of any one of embodiments 9-14, further comprising flushing the plurality of reaction vessels with a dry inert gas.

Embodiment 16. The method of any one of embodiments 9-15, wherein the method is executed by a computer.

Embodiment 17. The method of any one of embodiments 9-16, wherein more than two biopolymers are synthesized in parallel.

Embodiment 18. The method of any one of embodiments 9-17, wherein at least 96 biopolymers are synthesized in parallel.

Embodiment 19. The method of any one of embodiments 9-18, wherein at least 128 biopolymers are synthesized in parallel.

Embodiment 20. The method of any one of embodiments 9-19, wherein at least 1000 biopolymers are synthesized in parallel.

Embodiment 21. The method of any one of embodiments 9-20, wherein the biopolymer is an oligonucleotide.

Embodiment 22. The method of embodiment 21, wherein the oligonucleotide comprises a plurality of RNA nucleotides.

Embodiment 23. The method of embodiment 21, wherein the oligonucleotide comprises a plurality of DNA nucleotides.

Embodiment 24. The method of any one of embodiments 9-19, wherein the first solution comprises a peptide monomer.

Embodiment 25. The method of embodiment 24, wherein the biopolymer is an oligopeptide.

Embodiment 26. An automated computer-controlled multiplex biopolymer synthesizer for the stepwise production of an oligonucleotide of at least 100 nucleotides in length, wherein the average stepwise yield (ASWY) for the oligonucleotide is greater than 98%, 98.5%, 99%, 99.2%, 99.5%, or 99.6%.

Embodiment 27. The biopolymer synthesizer of embodiment 26, comprising a closed system comprising a reagent supply system, a multi-vessel reaction plate, and a reagent control system.

Embodiment 28. The biopolymer synthesizer of embodiment 26 or embodiment 27, wherein each reaction vessel is independently and pneumatically actuatable by the computer such that the synthesizer is capable of simultaneous delivery of a reagent to each reaction vessel.

Embodiment 29. A computer-controlled system for simultaneously synthesizing a plurality of molecules in parallel using a plurality of reagents, wherein the system is configured to pneumatically deliver a first reagent of the plurality of reagents to a plurality of reaction vessels, wherein the first reagent is delivered in or as a liquid.

Embodiment 30. The system of embodiment 29, wherein the system is configured to:
pneumatically displace, in each of the plurality of reaction vessels, the first reagent of the plurality of reagents in both a first direction and a second direction that is opposite the first direction, thereby promoting mixing within each of the plurality of reaction vessels; and
expel the first reagent from the system.

Embodiment 31. The system of embodiment 29 or embodiment 30, wherein the system is configured to pneumatically deliver the first reagent to the plurality of reaction vessels, pneumatically displace the first reagent of the plurality of reagents to promote mixing within each of the plurality of reaction vessels, and pneumatically expel the first reagent from the system without exposing the first reagent to the ambient environment prior to expulsion of the reagent from the system.

Embodiment 32. The system of any one of embodiments 29-31, wherein the system is configured to:
pneumatically deliver each of the plurality of reagents to the plurality of reaction vessels, wherein each reagent is delivered in or as a liquid; and
pneumatically displace, in each of the reaction vessels, each reagent of the plurality of reagents to promote mixing within each of the plurality of reaction vessels.

Embodiment 33. The system of any one of embodiments 29-32, wherein a reagent of the plurality of reagents is a phosphoramidite.

Embodiment 34. The system of embodiment 33, wherein a reagent of the plurality of reagents is a deprotecting agent, a capping agent, an activator for phosphoramidite coupling, or an oxidation agent.

Embodiment 35. The system of any one of embodiments 29-34, wherein the system is configured to selectively deliver, in a substantially simultaneous manner, the first reagent to a subset of the plurality of reaction vessels.

Embodiment 36. The system of any one of embodiments 29-35, further comprising a reagent supply system, wherein the system is configured such that the computer varies an amount of reagent delivered from the reagent supply system based on a number of reaction vessels in the subset of the plurality of reaction vessels.

Embodiment 37. The system of any one of embodiments 29-36, wherein each reaction vessel comprises a first porous surface (e.g., a first frit) and a second porous surface (e.g., a second frit), wherein the system is configured to initially deliver the first reagent to the plurality of reaction vessels though the first porous surface of each reaction vessel.

Embodiment 38. The system of embodiment 37, wherein the system is configured to expel first reagent from the system by delivering one or both of a wash solution and an inert gas through the second porous surface and the first porous surface, wherein the one or both of the wash solution and the inert gas contacts the second porous surface prior to contact with the first porous surface.

Embodiment 39. The system of any one of embodiments 37-38, the first reagent is initially delivered through the first porous surface in a direction that opposes a net gravitational force.

Embodiment 40. The system of any one of embodiments 29-39, wherein the plurality of molecules comprises an oligonucleotide.

Embodiment 41. An automated computer-controlled multiplex biopolymer synthesizer comprising a multi-vessel reaction plate comprising a plurality of reaction vessels, each reaction vessel coupled to (i) a reagent supply module comprising one or more reagents and (ii) a vacuum source or pressure source, such that each reaction vessel is independently and pneumatically actuatable by the computer such that the synthesizer is capable of synthesizing, in parallel, a different biopolymer in each of the plurality of reaction vessels.

Embodiment 42. The biopolymer synthesizer of embodiment 41, wherein the synthesizer is configured to:
simultaneously deliver one or more reagents to each of the reaction vessels; and
simultaneously remove the one or more reagents from each of the reaction vessels.

Embodiment 43. The biopolymer synthesizer of embodiment 41 or embodiment 42, wherein each of the plurality of reaction vessels in the multi-vessel reaction plate is a channel with an open top and bottom and a pair of filters that enables all reagents and solvents to pass through freely.

Embodiment 44. The biopolymer synthesizer of embodiment 43, further comprising a solid support material (SSM) between the pair of filters enabling solid-phase synthesis reaction to occur thereon.

Embodiment 45. The biopolymer synthesizer of embodiment 43, wherein the solid-phase synthesis comprises peptide synthesis, oligonucleotide synthesis, oligosaccharide synthesis or combinatorial chemistry.

Embodiment 46. The biopolymer synthesizer of any one of embodiments 43-45, wherein the SSM comprise particles of 50-200 μM in diameter.

Embodiment 47. The biopolymer synthesizer of any one of embodiments 32-46, wherein the SSM comprise controlled pore glass (CPG) or polystyrene.

Embodiment 48. The biopolymer synthesizer of any one of embodiments 41-47, wherein the multi-vessel reaction plate is thermally conductive.

Embodiment 49. The biopolymer synthesizer of any one of embodiments 41-48, wherein the multi-vessel reaction plate comprises aluminum or stainless steel.

Embodiment 50. The biopolymer synthesizer any one of embodiments 41-49, wherein the multi-vessel reaction plate is removable from the synthesizer.

Embodiment 51. A multiplex synthesizer configured to simultaneously synthesize a plurality of different reactions by pneumatically delivering and displacing each reagent used in the synthesis.

Embodiment 52. A multiplex synthesizer comprising a plurality of reaction vessels, wherein each reaction vessel contains solid support media, and wherein the synthesizer is configured to pneumatically deliver one or more reagents to each of the reaction vessels.

Embodiment 53. The synthesizer of embodiment 50, wherein the solid-phase medium comprises controlled pore glass.

Embodiment 54. The synthesizer of embodiment 50, wherein the solid-phase medium comprises polystyrene.

Embodiment 55. The synthesizer of any one of embodiments 52-54, wherein each reaction vessel comprises a first frit and a second frit, wherein the solid-phase medium is disposed between a first frit and the second frit.

Embodiment 56. An automated computer controlled multiplex biopolymer synthesizer configured to simultaneously activate fluid delivery, fluid removal, agitation, or cleaning in at least 100, 200, 500, or 1,000 different reaction vessels in a multi-vessel reaction plate.

Embodiment 57. The biopolymer synthesizer of embodiment 56, wherein each reaction vessel comprises two filters separating a reaction volume comprising SSM, wherein the reaction volume is between 15 and 100 microliters.

Embodiment 58. The synthesizer of embodiment 56 or embodiment 57, wherein the system lacks an XY stage for delivering the first reagent to the plurality of reaction vessels.

Embodiment 59. The system of any one of embodiments 56-58, wherein the system is configured to result in an increase of the speed of parallel synthesis relative to an embodiment that uses an XY stage for delivery of reagent to a plurality of reaction vessels.

Embodiment 60. The system any one of embodiments 56-59, wherein the system is configured to result in a decrease of process variability relative to an embodiment that uses an XY stage for delivery of reagent to a plurality of reaction vessels.

Embodiment 61. A method for multiplex synthesizing of a plurality of different biopolymers comprising:
  pneumatically and simultaneously, delivering reagents to selective subsets of reaction vessels of a multi-vessel cartridge in a cyclic fashion such that at each successive cycle any of the following parameters is adjustable:
    (i) the reagent delivered;
    (ii) the subset of reaction vessels the reagent is delivered to;
    (iii) the amount of time the reagent is permitted to incubate in the reaction vessel;
    (iv) the amount of reagent delivered; and/or
    (v) the temperature of the multi-vessel cartridge;
  wherein the multi-vessel cartridge comprises at least 96 reaction vessels.

Embodiment 62. A multiplex biopolymer synthesizer configured for having a cycle time of less than one hour (e.g., less than 45 minutes, less than 30 minutes, less than 15 minutes, less than 10 minutes, or less than 8 minutes), wherein a cycle comprises a deprotection step, four coupling steps (e.g., one for each phosphoramidite monomer), a capping step, and an oxidation step.

Embodiment 63. The multiplex biopolymer synthesizer of embodiment 62, wherein the coupling step is less than three minute, less than two minutes, less than 1.5 minutes, less than one minute, less than 0.5 minutes, or less than 0.25 minutes.

Embodiment 64. The multiplex biopolymer synthesizer of embodiment 62 or embodiments 63, comprising a temperature controllable multi-vessel reaction plate and a pneumatically activated system for fluid delivery, fluid removal, agitation, or cleaning.

Embodiment 65. The multiplex biopolymer synthesizer of embodiment 64, wherein the multi-vessel reaction plate is configured to heat up to at least 35° C., 40° C., 50° C., or 55° C. (e.g., a multi-vessel reaction plate configured to heat from room temperature up to 80° C.).

Embodiment 66. A multiplex biopolymer synthesizer configured for synthesizing a plurality of different 20-mer biopolymers (e.g., RNA polymers) in less than 250, less than 200, or less than 160 minutes with a yield of at least 90%, at least 92%, or at least 95%.

Embodiment 67. A system configured for performing solid-phase synthesis of a plurality of different polymers, each in a different reaction vessel, wherein the reaction vessels are disposed within or defined by a temperature-controlled reaction plate.

Embodiment 68. The system of embodiment 67, wherein the reaction plate is at a temperature that differs from ambient temperature.

Embodiment 69. The system of embodiment 67 or embodiment 68, wherein the temperature-controlled reaction plate is at a temperature of between 35° C. and 65° C.

Embodiment 70. The system of any one of embodiments 67-69, wherein the temperature-controlled reaction plate is a metal plate.

Embodiment 71. A method for simultaneously synthesizing a plurality of different polymers in parallel with increased speed, the method comprising:
  providing a plurality of SSM in each of a plurality of reaction vessels;
  selectively introducing a first solution comprising a first monomer into a subset of the plurality of reaction vessels, thereby reacting the first monomer with an active moiety attached to the SSM; and
  adjusting temperature of the plurality of reaction vessels, thereby increasing reaction rate within each of said plurality of reaction vessels.

Embodiment 72. The method of embodiment 71, wherein the temperature is adjusted such that a first synthetic step is carried out at a first temperature and a second reaction step is carried out at a second temperature.

Embodiment 73. A method for simultaneously synthesizing a plurality of different polymers in parallel with increased speed comprising:
　providing a plurality of SSM in each of a plurality of reaction vessels;
　synthesizing a different oligomer in each of the plurality of reaction vessels by performing cycles of extension reactions, wherein each cycle:
　(i) comprises a deprotection step, four coupling steps (e.g., one for each phosphoramidite monomer), a capping step, and an oxidation step; and
　(ii) has a cycle time of less than one hour, less than 45 minutes, less than 30 minutes, less than 15 minutes, or less than 8 minutes.

Embodiment 74. A synthesizer comprising a plurality of reaction vessels and a reagent control system configured for simultaneously and independently delivering a controlled volume of liquid without the use of gravity to each of said plurality of reaction vessels.

Embodiment 75. The synthesizer of embodiment 74, wherein the reagent control system results in fluid delivery in an upwards vertical direction.

Embodiment 76. The synthesizer of embodiment 74 or embodiment 75, wherein the reagent control system is configured to deliver a fluid column to the reaction vessel.

Embodiment 77. The synthesizer of any one of embodiments 74-76, wherein the fluid column contacts all reactants within the reaction vessel such that no gas is in contact with any of the reactants.

Embodiment 78. The synthesizer of embodiment 77, wherein the reactants are loaded upon a SSM.

Embodiment 79. A system for performing a plurality of different reactions in parallel, each in a separate reaction vessel, wherein the system is configured to pneumatically deliver a first reagent in a solution to each of the plurality of reaction vessels such that each reaction vessel is completely filled with the solution.

Embodiment 80. The system of embodiment 79, wherein the first reagent is initially delivered into each of the separate reaction vessels in a direction that opposes the net gravitational force on solid phase media disposed within each of the plurality of reaction vessels.

Embodiment 81. The system of embodiment 79 or embodiment 80, wherein the system is configured to fully displace, with liquid, all gas within a solid support media that is disposed within each reaction vessel.

Embodiment 82. The system of any one of embodiments 79-81, wherein the system is configured to fully displace, with gas, all liquid within each reaction vessel.

Embodiment 83. A pneumatically actuatable multiplex synthesizer configured for providing pressure differentials to selectively agitate fluid in a plurality of reaction vessels without displacing the reaction vessels.

Embodiment 84. The synthesizer of embodiment 83, wherein the plurality of reaction vessels agitated comprise all of the reaction vessels in a multi-vessel reaction plate situated between the reagent activation system and the reagent supply system.

Embodiment 85. The synthesizer of embodiment 83, wherein the plurality of reaction vessels agitated comprise a subset of the reaction vessels in a multi-vessel reaction plate situated between the reagent activation system and the reagent supply system.

Embodiment 86. A system for performing a plurality of different reactions in parallel, each in a separate reaction vessel, wherein the system is configured to pneumatically (1) deliver a first column of liquid to solid phase media disposed within each reaction vessel and (2) alternate the direction of fluid flow through each reaction vessel, thereby agitating the solid phase media disposed therein.

Embodiment 87. The system of embodiment 86, wherein the reaction vessel comprises a first porous surface and a second porous surface, wherein at least a portion of the column of liquid passes through the first porous surface and the second porous surface during agitation.

Embodiment 88. The system of embodiment 86, wherein the first porous surface and the second porous surface are frits.

Embodiment 89. The system of any one of embodiments 86-88, wherein the plurality of reactions involve polymer elongation, and wherein during agitation, the solid phase media is exposed to between 1.3-fold and 20-fold excess of monomer relative to the number of sites for polymer elongation.

Embodiment 90. The system of embodiment 86, wherein the system is configured to alternate the direction of fluid flow at least two, at least three, at least four, or at least 5 times.

Embodiment 91. The system of any one of embodiments 86-89, a first direction of fluid flow is upward, and a second direction of fluid flow is downward.

Embodiment 92. The system of any one of embodiments 86-91, wherein the system is a computer-controlled system.

Embodiment 93. A method for flushing out a plurality of reaction channels simultaneously comprising: using a pressure differential to deliver a fluid column of a solvent to each of a plurality of reaction volumes, wherein each of the reaction volumes is positioned in one of the plurality of reaction channels, and
　using a pressure differential to remove the solvent from each of the reaction volumes.

Embodiment 94. The method of embodiment 93, wherein the fluid column is delivered without the use of gravity.

Embodiment 95. The method of embodiment 93 or embodiment 94, wherein the solvent is acetonitrile.

Embodiment 96. The method of any one of embodiments 93-95, wherein the removing is performed by delivering pressurized nitrogen to the reaction vessel.

Embodiment 97. A computer-controlled system for performing a plurality of different reactions in parallel, each in a separate reaction vessel, wherein the system comprises:
　a reagent supply system for delivering a plurality of reagents to a plurality of reaction vessels that contain solid support media disposed therein; and
　a wash system for delivering a wash fluid to the plurality of reaction vessels, wherein the wash system is configured to fill the reaction vessels with wash fluid.

Embodiment 98. The system of embodiment 97, wherein the wash system is configured to simultaneously deliver wash fluid to each of the reaction vessels.

Embodiment 99. The system of embodiment 97 or embodiment 98, wherein the wash fluid is pneumatically delivered through the reaction vessels.

Embodiment 100. A system for synthesizing a polymer, the system comprising:
　a reagent supply system;
　a first manifold coupled to the reagent supply system;
　a plurality of reaction vessels coupled to the first manifold, wherein each reaction vessel of the plurality of reaction vessels comprises a first porous membrane, a second porous membrane, and a region disposed between the first porous membrane and second porous membrane for containing a solid support medium;

a reagent control system coupled to the plurality of vessels, wherein the reagent control system is configured to selectively deliver reagent originating from the reagent supply system to a first subset of the plurality of reaction vessels; and an outlet port coupled to the first manifold;

wherein the system is configured such that reagent from the reagent supply system passes through the system to the outlet port without contacting the ambient environment.

Embodiment 101. The system of embodiment 100, further comprising a wash system coupled to the plurality of reaction vessels, wherein the wash system is configured to deliver wash fluid through each of the plurality of reaction vessels to exit from the outlet port.

Embodiment 102. The system of embodiment 101, wherein wash fluid from the wash system enters into the reaction vessel through the second porous membrane and the first reagent initially enters into the reaction vessel through the first porous membrane.

Embodiment 103. The system of any one of embodiments 100-102, wherein each reaction vessel of the plurality of reaction vessels is orientated such that the first porous membrane is disposed below the second porous membrane.

Embodiment 104. The system of any one of embodiments 100-103, further comprising a plurality of branched connectors, wherein each branched connector couples a reaction vessel of the plurality of reaction vessels to the wash system and reagent control system.

Embodiment 105. The system of any one of embodiment 100-104, further comprising a second manifold that includes the branched connector.

Embodiment 106. The system of any one of embodiments 100-105, wherein the wash system further comprises a compressed inert gas, and wherein the wash system is configured to cause the flow of inert gas through each of the plurality of reaction vessels to exit from the outlet port.

Embodiment 107. The system of any one of embodiments 100-106, wherein the system is configured such that, in operation, the system carries out a reagent delivery step, a reaction step, and a reagent wash step.

Embodiment 108. The system of embodiment 107, wherein the reagent delivery step comprises:

flowing reagent from the reagent supply system through the first manifold; and drawing the first reagent through the first porous membrane of the subset of the plurality of reaction vessels into the region for containing the solid support medium.

Embodiment 109. The system of embodiment 107 or embodiment 108, wherein the reaction step comprises repeatedly displacing the first reagent across the subset of reaction vessels.

Embodiment 110. The system of any one of embodiments 107-109, wherein the reagent wash step comprises delivering a wash fluid through the second porous membrane into the plurality of reaction vessels, through the first manifold to exit the outlet port.

Embodiment 111. The system of any one of embodiments 100-110, wherein each reagent of the plurality of reagents is pressurized within a container.

Embodiment 112. The system of any one of embodiments 100-111, wherein the reagent control system is substantially devoid of wash fluid or first reagent throughout operation of the system.

Embodiment 113. The system of any one of embodiments 100-112, further comprising a reaction plate that contains and/or defines the plurality of reaction vessels.

Embodiment 114. The system of embodiment 113, wherein the reaction plate is temperature-controlled.

Embodiment 115. The system of embodiment 113 or embodiment 114, wherein the reaction plate comprises a keyed registration feature.

Embodiment 116. The system of any one of embodiments 100-115, wherein the first manifold comprises a common interior lumen that is in fluid communication with all fluid in the manifold.

Embodiment 117. The system of any one of embodiments 100-116, wherein the reagent control system comprises a pressure selector.

Embodiment 118. The system of any one of embodiments 100-117, wherein the system does not include an inert gas blanket that flows inert gas out of the system through an opening other than the outlet port coupled to the first manifold.

Embodiment 119. The system of any one of embodiments 100-118, wherein the system is configured to pneumatically drive all reagents from the reagent supply system to the subset of reaction vessels of the plurality of reaction vessels and then expel the reagents from the system through the outlet port.

Embodiment 120. The system of any one of embodiments 100-119, wherein, in operation, the plurality of reaction vessels are spatially fixed relative to the reagent supply system.

Embodiment 121. A computer program product configured to operate the system or carry out the method of any of embodiments 1-120.

Embodiment 122. A method for synthesizing a plurality of different oligonucleotides that each comprise a first oligonucleotide segment and a second oligonucleotide segment, the method comprising synthesizing, in each of a plurality of reaction vessels, a second oligonucleotide segment onto a first oligonucleotide segment that is attached to solid support media, wherein first oligonucleotide segment is identical between each of the plurality of different oligonucleotides, and the second oligonucleotide segment differs between each of the plurality of different oligonucleotides.

Embodiment 123. The method of embodiment 122, further comprising, prior to synthesizing the second oligonucleotide segment onto the first oligonucleotide segment, transferring different portions of a single source of solid-phase media to each of the plurality of reaction vessels, wherein, at the time of transfer, the solid phase media is attached to the first oligonucleotide segment.

Embodiment 124. The method of embodiment 122 or embodiment 123, further comprising, prior to transferring different portions of the single source of solid-phase media to each of the plurality of reaction vessels, synthesizing a first oligonucleotide segment on solid-phase media.

Embodiment 125. The method of any one of embodiments 122-124, wherein the first oligonucleotide segment is synthesized on a first oligonucleotide synthesizer and the second oligonucleotide segment is synthesized on a second oligonucleotide synthesizer.

Embodiment 126. The method of any one of embodiments 122-125, wherein the plurality of reaction vessels are formed from a single reaction plate.

Embodiment 127. The method of any one of embodiments 122-126, wherein the second oligonucleotide segment is positioned 5' to the first oligonucleotide segment.

Embodiment 128. The method of any one of embodiments 122-127, wherein the second oligonucleotide segment is synthesized onto the first oligonucleotide segment via phosphoramidite chemistry.

Embodiment 129. The method of any one of embodiments 122-128, wherein the plurality of oligonucleotides comprise CRISPR guide RNAs.

Embodiment 130. The method of any one of embodiments 122-129, wherein synthesizing the second oligonucleotide segment onto the first oligonucleotide segment comprises adding phosphoramidite monomers to the first oligonucleotide to form the second oligonucleotide segment.

Embodiment 131. The method of any one of embodiments 122-130, wherein synthesizing the second oligonucleotide segment onto the first oligonucleotide segment comprises conjugating an oligomer comprising the second oligonucleotide segment to the first oligonucleotide segment.

Embodiment 132. The method of embodiment 131, wherein conjugating the oligomer to the first oligonucleotide segment does not involve phosphoramidite chemistry.

Embodiment 133. The method of any one of embodiments 122-132, wherein the second oligonucleotide segment is between 2 and 150 nucleotides in length.

Embodiment 134. The method of any one of embodiments 122-133, wherein the second oligonucleotide segment is between 17 and 22 nucleotides in length.

Embodiment 135. The method of any one of embodiments 122-134, wherein the second oligonucleotide segment is 20 nucleotides in length.

Embodiment 136. The method of any one of embodiments 122-135, further comprising cleaving the plurality of oligonucleotides from the solid-phase media.

Embodiment 137. A method for synthesizing a plurality of different oligonucleotides that each comprise a first oligonucleotide segment and a second oligonucleotide segment, the method comprising:
synthesizing, on a first oligonucleotide synthesizer, a first oligonucleotide segment on solid-phase media within each of a plurality of reaction vessels of a reaction plate;
transferring the reaction plate to a second oligonucleotide synthesizer; and
synthesizing, in each of the plurality of reaction vessels, a second oligonucleotide segment onto the first oligonucleotide segment;
wherein first oligonucleotide segment differs between each of the plurality of different oligonucleotides, and the second oligonucleotide segment is identical between each of the plurality of different oligonucleotides.

Embodiment 138. The method of embodiment 137, wherein the second oligonucleotide segment is positioned 5' to the first oligonucleotide segment.

Embodiment 139. The method of embodiment 137 or embodiment 138, wherein synthesizing the second oligonucleotide segment onto the first oligonucleotide segment comprises adding phosphoramidite monomers to the first oligonucleotide to form the second oligonucleotide segment.

Embodiment 140. The method of any one of embodiments 137-139, wherein synthesizing the second oligonucleotide segment onto the first oligonucleotide segment comprises conjugating an oligomer comprising the second oligonucleotide segment to the first oligonucleotide segment.

Embodiment 141. The method of embodiment 140, wherein conjugating the oligomer to the first oligonucleotide segment does not involve phosphoramidite chemistry.

Embodiment 142. The method of any one of embodiments 137-141, further comprising cleaving the plurality of oligonucleotides from the solid-phase media.

Embodiment 143. The method of any one of embodiments 137-142, wherein the second oligonucleotide segment is positioned 3' to the first oligonucleotide segment.

Embodiment 144. The method of embodiment 143, wherein the plurality of different oligonucleotides are formed from 5' to 3' phosphoramidites.

Embodiment 145. A method for synthesizing a plurality of different oligonucleotides that each comprise a first oligonucleotide segment and a second oligonucleotide segment, the method comprising:
synthesizing, with a first oligonucleotide synthesizer, a first oligonucleotide segment on solid-phase media within each of a plurality of reaction vessels of a reaction plate;
transferring the reaction plate to a second oligonucleotide synthesizer; and
synthesizing, in each of the plurality of reaction vessels, a second oligonucleotide segment onto the first oligonucleotide segment;
wherein either the first segment or the second segment comprises one or more modified or labelled nucleotides, and the other segment lacks both modified and labelled nucleotides.

Embodiment 146. The method of embodiment 145, wherein second oligonucleotide segment is positioned 5' to the first oligonucleotide segment.

Embodiment 147. The method of embodiment 145 or embodiment 146, wherein the second oligonucleotide segment is between 17 and 22 nucleotides in length.

Embodiment 148. The method of any one of embodiments 145-147, wherein the second oligonucleotide segment is 20 nucleotides in length.

Embodiment 149. The method of any one of embodiments 145-148, wherein the modified or labelled nucleotides are incorporated into the second oligonucleotide segment.

Embodiment 150. The method of any one of embodiments 145-149, wherein the modified or labelled nucleotides are incorporated into the first oligonucleotide segment.

Embodiment 151. The method of any one of embodiments 145-150, wherein the plurality of oligonucleotides comprise CRISPR guide RNAs.

Embodiment 152. The method of any one of embodiments 145-152, wherein synthesizing the second oligonucleotide segment onto the first oligonucleotide segment comprises adding phosphoramidite monomers to the first oligonucleotide to form the second oligonucleotide segment.

Embodiment 153. The method of embodiment 145, further comprising cleaving the plurality of oligonucleotides from the solid-phase media.

Embodiment 154 A multiplex biopolymer synthesizer comprising:
a) a reagent supply system (316),
wherein the reagent supply system (316) is configured to deliver a plurality of reagents to the multi-vessel reaction plate (100);
b) a multi-vessel reaction plate (100),
wherein each vessel of the multi-vessel reaction plate (100) comprises solid support media (SSM);
wherein each vessel of the multi-vessel reaction plate (100) is independently and pneumatically actuatable;
c) a reagent control system (310) comprising a pressure selector system (394) and a wash system (390);
wherein the pressure selector system (394) is configured to effect variable pressure either with or against the direction of flow from the reagent supply system (316) at each of the reaction vessels (110) of the reaction plate (100) thereby selectively agitating fluid in each of the reaction vessels (110) independently, without displacing the reaction vessels (110);
wherein the wash system (390) is configured to deliver (optionally in a simultaneous manner) wash fluid to each of the reaction vessels (110) (optionally independently), thereby expelling the reagents from the reaction vessels (110); and d) a drain system (318) having an outlet port configured to remove reagents from the synthesizer;
wherein the reagent supply system (316), the multi-vessel reaction plate (100), and the reagent control system (310) form a closed system during biopolymer elongation.

Embodiment 155. The biopolymer synthesizer of embodiment 154, wherein the multi-vessel reaction plate (100) is removable from the synthesizer.

Embodiment 156. The multiplex biopolymer synthesizer according to embodiment 154 or 155, wherein the synthesizer further comprises a first manifold (312) and a second manifold (314) configured to clamp the multi-vessel reaction plate (100) in between, thereby creating a seal.

Embodiment 157. The multiplex biopolymer synthesizer according to embodiment 156, wherein one of the manifolds (312) is coupled to the reagent control system (310) and the other manifold (314) is coupled to the reagent supply system (316).

Embodiment 158. The multiplex biopolymer synthesizer according to any one of embodiments 154-157, wherein the multi-vessel reaction plate (100) is temperature-controlled by means of a heater actuator (356) and a temperature control system (354).

Embodiment 159. The multiplex biopolymer synthesizer according to any one of embodiments 154-158, wherein the drain system (318) is configured to supply variable back-pressure opposing the flow from the wash system (390) of the reagent control system (310) to allow for agitation and/or pneumatic displacement of reagent or wash solution within the reaction vessels (110) of the reaction plate (100).

Embodiment 160. The multiplex biopolymer synthesizer according to any one of embodiments 154-159, wherein the reagent control system (310) creates negative pressure at a subset or all of the reaction vessels (110) and the reagent supply system (316) delivers reagents to a subset or all of the reaction vessels (110), thereby allowing that reagents to reach the other end of the subset or all of the reaction vessels (110) of the reaction plate (100), thereby saturating the SSM.

Embodiment 161. The multiplex biopolymer synthesizer according to any one of embodiments 154-160, wherein said synthesizer is controlled by a computer.

Embodiment 162. A multi-vessel reaction plate (100) comprising
a) a plurality of independently and pneumatically actuatable vessels (110), wherein each or most of the vessels (110) comprise solid support media and optionally one or more filters,
b) a first surface (102)
c) a second surface (104),
d) a flange (106),
e) optionally a step (108) configured to be keyed into the multiplex biopolymer synthesizer of any one of the preceding embodiments;
where said plurality of vessels (110) are provided as cylindrical lumens within the reaction plate (100) which pass from the first surface (102) to the second surface (104).

Embodiment 163. A method for multiplex synthesis of a plurality of biopolymers, the method comprising:
obtaining the multiplex biopolymer synthesizer according to any one of embodiments 154-162;
selectively delivering a first solution to a first subset of the plurality of reaction vessels such that the first solution contacts the solid phase resin disposed therein but does not enter into reaction vessels of the plurality of reaction vessels that are not within the first subset; and
ejecting the first solution from the first subset of reaction vessels to an outlet port, wherein the first solution is not exposed to ambient moisture prior to ejection from the outlet port.

Embodiment 164. The method of embodiment 163, further comprising selectively delivering a second solution into a second subset of the plurality of reaction vessels such that the second solution contacts solid phase resin disposed therein, wherein the second subset of the plurality of reactions vessels differs from the first subset of the plurality of reaction vessels.

Embodiment 165. The method of embodiment 163 or 164, wherein the first solution is simultaneously delivered into each of the reaction vessels of the first subset of the plurality of reaction vessels.

Embodiment 166. The method of any one of embodiments 163-165, further comprising washing the plurality of reactions vessels with a wash fluid or flushing the plurality of reaction vessels with a dry inert gas.

Embodiment 167. The method of any one of embodiments 163-166, further comprising adjusting any one of the following parameters:
(i) the reagent delivered;
(ii) the subset of reaction vessels the reagent is delivered to;
(iii) the amount of time the reagent is permitted to incubate in the reaction vessel;
(iv) the amount of reagent delivered; and/or
(v) the temperature of the multi-vessel cartridge.

Embodiment 168. A computer program adapted to perform the steps of the methods and systems according to any one of embodiments 154-167, when run on a computer.

The following description is of various embodiments of the present invention selected to illustrate principles and application of the invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the set of drawings in which the reference number first appears.

I. Definitions

"SSM" or "solid support media" is used herein interchangeably with "solid-phase media" or "solid-phase resin" and is intended to refer to any of a variety of solid particulate media containing chemically modifiable groups suitable for covalent attachment of polymers thereto. An example is controlled-pore glass (CPG), which is used for oligonucleotide synthesis.

"Ambient environment" is used herein to refer to the gaseous mixture external to the systems described herein. In some embodiments, the systems are benchtop systems operating in an open laboratory, in which case the ambient environment refers to air external to the device itself. In some embodiments, the systems are operated in an altered environment (e.g. a clean room, or under an inert gas blanket) in which case the ambient environment refers to the altered atmosphere (e.g. HEPA-filtered air, nitrogen, or argon) external to the device.

"Deprotection" is used herein interchangeably with "deblocking" and is intended to refer to the removal of protecting groups from nucleophilic moieties (e.g. hydroxyl groups, thiol groups, amine groups) present on molecules described herein.

II. Overview

Described herein are systems, devices, and methods that enable automated, rapid, highly-consistent, high-yield, multiplex (>96, >128, >264, >512, or >1000 channel) synthesis of polymeric molecules (e.g. biomolecules such as oligonucleotides) on solid phase media. In one embodiment, the present disclosure provides for a pneumatic, multichannel synthesizer with a reagent supply system and individually-actuatable, temperature-controlled solid phase channels wherein the entire system is closed to the ambient environment and pressurized with inert gas. The combination of the reagent supply system with individually actuatable channels enables easy scalability according to device footprint limitations and desired yield (e.g. amount of solid phase) per channel. Temperature control and pneumatic delivery of reagents to the solid phase allows for accelerated reaction rate and rapid cycling for deprotection, chain elongation, oxidation, and capping steps. Isolation of the entire synthesis system from the ambient environment and under pressurized inert gas minimizes (e.g. for oligonucleotide synthesis) inactivation of phosphoramidite monomers or activated tetrazolides prior to delivery to the solid phase resin, improving stepwise coupling yield. For solid phase peptide synthesis, isolation of the entire synthesis system from the ambient environment (moisture, air) minimizes e.g. oxidation of amino acid monomers (free or incorporated into the growing chain) and hydrolysis of the growing peptide chain.

III. Organization and Interfunctionality of Synthesizer Architecture

Figure 3A:
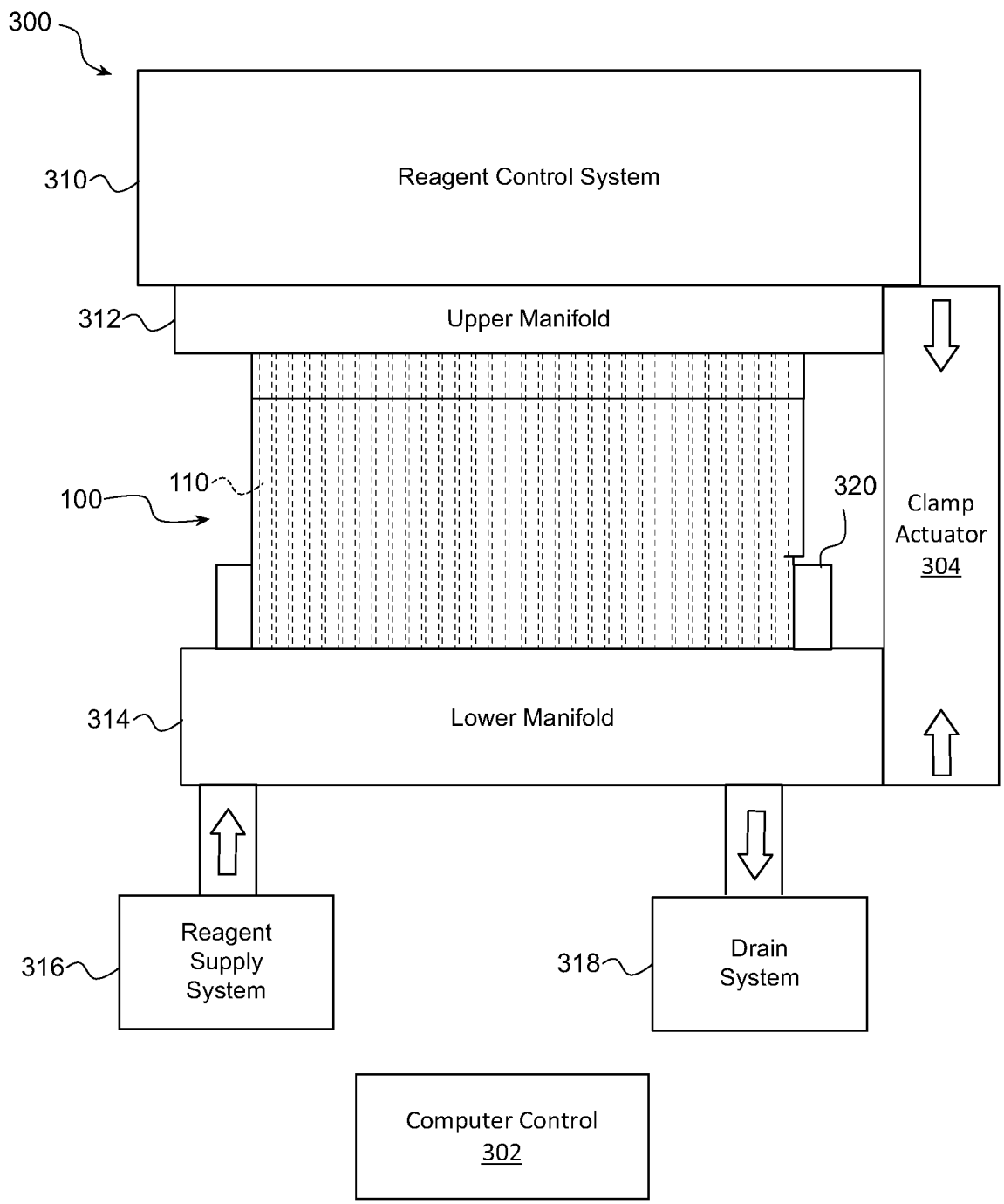
FIGS. 3A and 3B show views of a multi-channel oligonucleotide synthesizer.

FIG. 3A illustrates how modules may be organized in practice to produce a synthesizer or system 300 with all these beneficial features, which in some embodiments is computer-controlled. First, a pneumatically-driven reagent supply system 316 is in fluid communication with a lower or first manifold 314, which in turn is in fluid communication with a plurality of channels/reactions vessel 110 of a reaction plate (i.e. "multi-vessel reaction plate") 100 via a first face of the reaction plate 100 which contain solid support media (SSM) to which the polymers are tethered during synthesis. The plurality of channels/reaction vessels of the reaction plate 100 are thus spatially fixed relative to the reagent supply system. The lower (or first) manifold 314 comprises a common interior lumen that is in fluid communication with all fluid in the manifold. The channels/reaction vessels 110 of the reaction plate 100 are supplied with solid support medium (SSM). The combination of the reagent supply system 316 and the lower manifold 314, enables simultaneous delivery of reagents to the plurality of channels/reaction vessels of the reaction plate 100. Because the system is pneumatically-driven, delivery of reagents by the reagent supply system 316 to the channels/reaction vessels 110 can be in any orientation (e.g. counter to the direction of gravity, perpendicular to the direction of gravity, etc) and does not require gravity to deliver reagents to the solid phase/solid support media.

The reagent supply system 316 is configured to effect pneumatic delivery of reagents for each oligomer synthesis step. In the case of solid phase oligonucleotide synthesis (SPOS), the reagent supply system 316 may alternately deliver detritylation/deblocking (e.g. trichloroacetic acid in dichloromethane), chain elongation/coupling (e.g. phosphoramidite monomer/tetrazole in acetonitrile), capping (e.g. acetic anhydride/pyridine/THF and N-methylimidazole in acetonitrile), and oxidation (e.g. iodine in pyridine/THF) reagents. In the case of solid phase peptide synthesis (SPPS), the reagent supply system 316 may alternatively provide deprotection (e.g. pyridine/DMF) and chain elongation/coupling (e.g. Fmoc-amino acid-OH, HBTU, and DIEA in DMF) reagents.

Second, the plurality of channels/reaction vessels 110 of the reaction plate 100 are in fluid communication with an upper manifold 312 via a second face of the reaction plate 100. In some embodiments, the channels within the upper manifold 312 are in fluid communication with a branched subsystem 330 that connects to a wash system 390 and a pressure selector system 394 (see FIG. 3D). The wash system 390 may be configured to effect pneumatic delivery of one or more wash solvents 391 (e.g., acetonitrile for SOPS and DMF for SPPS) or inert gas 392 (e.g., nitrogen or argon) to be delivered in between synthesis steps (e.g. deprotection, coupling, oxidation). In some embodiments, the pressure selector system 394 is configured to effect variable pressure either with or against the direction of flow from the reagent supply system 316 at each of the channels/reaction vessels 110 of the reaction plate 100, and may be substantially devoid of wash and/or reagent solution throughout operation (e.g. it may not comprise an outlet port). In some embodiments, the variable pressure is accomplished via connection to a pressurized inert gas source and a vacuum source. The combination of flow from the reagent supply system and individually adjustable pressure (via the reagent control system 310) at the channels/reaction vessels 110 of the reaction plate 100 allows for selective delivery of reagents to a subset or all of the channels/reaction vessels 110 of the reaction plate 100. By providing flow of reagent from the reagent supply system 316 through the lower manifold 314 up to the bottom of the reaction plate 100 and creating negative pressure at a subset of the channels/reaction vessels 110 via the reagent control system 310, reagent flow can be modulated to reach the top of a subset of the channels/reaction vessels 110 and thus saturate the SSM therein. This process serves to pneumatically deliver the reagent (e.g. as or in a liquid) to a first subset of the reaction vessels without entering into reaction vessels 110 that are not within the subset. In a following step, the same process can then selectively deliver a second reagent solution from the reagent supply system into a second subset of the plurality of reaction vessels 110 that partially overlap or differ entirely from the first subset of reaction vessels 110. Alternatively, by providing negative pressure at all of the channels/reaction vessels 110, reagent flow can be modulated to reach the top of all of the channels/reaction vessels 110 and thus saturate all of the SSM in the reaction plate. In one embodiment the wash and agitate functionality are accomplished via the wash system 390 and the pressure selector system 394. For instance, one or more valves may provide a connection to either a positive pressure source or a vacuum source, and one or more other valves may provide a connection to solvent 391 (e.g. acetonitrile) and/or inert gas 392 (e.g. argon or nitrogen) for each channel/reaction vessel. In this embodiment, the vertical position of reagent and/or solvent contained in each channel/reaction vessel 110 may be controlled by optimizing the length of time the channel 110 is connected to either vacuum or the pressure source as well as the pressures provided by the vacuum and positive pressure source. Similarly, the volume of wash reagent or inert gas may be controlled by varying the amount of time the channels/reaction vessels 110 are exposed to inert gas 392 or solvent 391.

Third, the entire system between the reagent supply system 316, the multi-channel/multi-vessel reaction plate 100, and the reagent control system 310 can be a closed system. In some embodiments, this is accomplished by pressurizing the reagent supply system (e.g. with an inert gas such as nitrogen or argon); this combination with the reagent control system (which can modulate pressure within the channels/reaction vessels via inert gas pressure and a vacuum) ensures that all of the synthesis operations up to addition of the terminal monomer of the polymer (e.g. all the steps of polymer elongation) can be accomplished without influx/interchange of ambient air with the environment external to the synthesizer. This ensures that all the reagents and nascent polymers within the synthesizer are protected from oxygen, moisture, and other contaminants from the ambient environment that may be detrimental to the synthetic steps. Thus, the automated synthesizer system described herein does not require the use of an inert gas "blanket" surrounding the exterior of the synthesizer apparatus to prevent exposure to air and/or moisture.

Fourth, the lower manifold 314 is connected to a drain system 318 having an outlet port, which serves to remove reagents provided by the reagent supply system once they have saturated the SSM in the channels/reaction vessels 110 of the reaction plate 100, and to wash the SSM in the channels/reaction vessels free of excess reagent. In some embodiments, once flow of reagents has saturated the SSM in the channels/reaction vessels 110 of the reaction plate 100, flow from the reagent supply system 316 is isolated, the drain system 318 is opened or connected, and flow of solvent or inert gas in the opposing direction is provided through the channels/reaction vessels 110 via the wash system 390 to expel the reagent from the channels/reaction vessels 110. This serves to simultaneously remove reagent solutions from the plurality of channels/reaction vessels of the reaction plate. As the wash system 390 can provide both solvent and inert gas flow, the wash system 390 can be used to both rinse and "dry" the SSM contained in the channels/reaction vessels 110. In the case of solutions provided by both the reagent supply system and the wash system 390, the closed architecture between the reagent/wash systems and the lower manifold/reaction plate/upper manifold along with the pneumatic delivery of the solutions serves to isolate the reagent and wash solutions from ambient moisture prior to ejection from the drain system/outlet port. Particularly, the synthesizer/synthesizer system is configured to prevent reagents from contact with moisture and/or oxygen from the external environment prior to expulsion of the reagents from the system. This minimizes any inactivation of the activated monomer or coupling reagents that may contribute to reduced overall yield. In various embodiments, the synthesizer system is configured such that the water content of a first reagent of the one or more reagents never exceeds 2, 5, 10, 20, or 30 ppm by weight until at least expulsion of the first reagent from the synthesizer system.

Figure 3B:
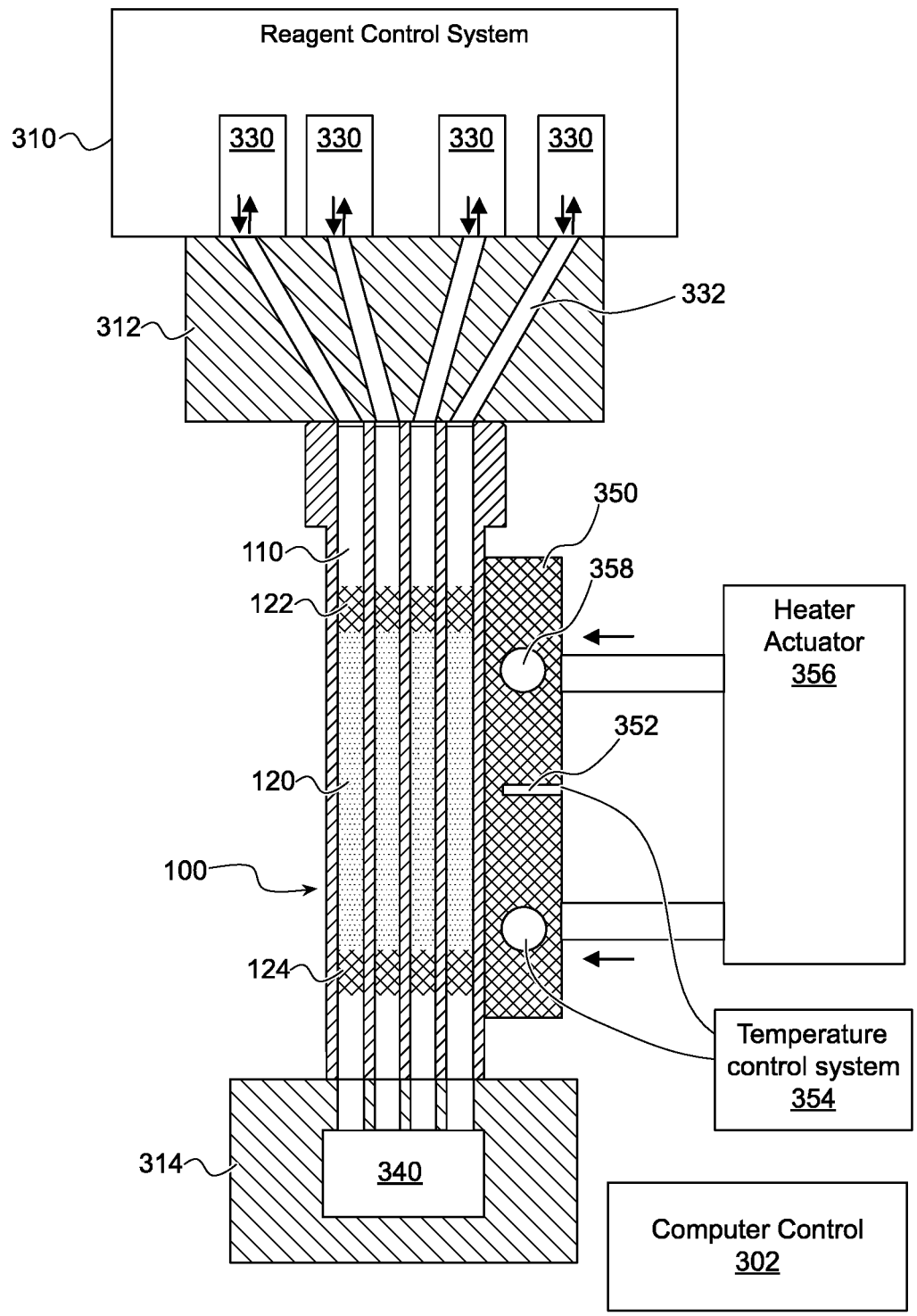

Fifth, the reaction plate 100 is thermally conductive and provided with temperature control to accelerate the rate of reaction of molecules attached to SSM within the channels/reaction vessels 110 of the reaction plate 100 with reagent. This is illustrated in FIG. 3B by the provision of a heater actuator 356 and a temperature control system 354 which are both in thermal communication with the reaction plate 100.

Sixth, the reaction plate 100 is removable and interchangeable. A clamp actuator 304 allows for contact between the lower and upper manifolds and the reaction plate to be connected/disconnected and the plate is held in physical alignment with lower and upper manifolds via registration features 320. Removal of the reaction plate 100 allows for changing of the identity or amount of the SSM (e.g. SSM preloaded with individual nucleotides or pre-synthesized oligonucleotides, different chemical structure of SSM, SSM suitable for peptide vs oligonucleotide synthesis). Modularity of the reaction plate 100 additionally allows for a multi-stage polymer synthesis protocol, wherein the initial parts of a polymer are synthesized attached to a solid phase which is then distributed to the channels/reaction vessels 110 of the reaction plate 100 and loaded into the synthesizer for further combinatorial derivatization.

Thus in a typical sequence of reagent supply to and removal from the SSM (which is optionally executed by a computer): 1) positive flow of solution from the reagent supply system 314 (which may be in an upwards vertical direction, or opposite the direction of the gravitational force,) and negative pressure via the reagent control system 310 are provided to deliver or draw a continuous fluid column (e.g. excluding gas) to completely fill the channels/reaction vessels 110 of the reaction plate 100 and saturate the SSM therein; 2) reaction temperature control (e.g. heating above room temperature to reaction optimal temp) is provided via controlled thermal input to the reaction plate via the heater actuator 356 and the temperature control system 354; and 3) flow from the reagent supply system 316 is isolated, the drain system 318 is opened or connected, and flow of solvent is provided from the wash system 390 to expel the reagent from the SSM and wash free reagent away from the SSM. This sequence serves to perform all the necessary reagent mixtures contacting the ambient environment. Thus, in a typical monomer addition cycle (which involves the same steps) according to the sequence above, the synthesizer system is able to selectively deliver a first solution from a source that is sealed off from ambient air to a first subset of the plurality of reaction vessels 110 such that the first solution contacts the SSM/solid phase resin disposed therein but does not enter into reaction vessels of the plurality of reaction vessels that are not within the first subset; and eject the first solution from the first subset of reaction vessels 110 to a drain system/outlet port, wherein the first solution is not exposed to ambient moisture prior to ejection from the outlet port. Further, via the same architecture and sequence, the synthesizer system is able to deliver a second solution into a second subset of the plurality of reaction vessels 110 such that the second solution contacts solid phase resin disposed therein, wherein the second subset of the plurality of reactions vessels 110 differs from the first subset of the plurality of reaction vessels. The first solution may be any of the solutions commonly used for polymer synthesis. For example, in the case when a preloaded resin is used, the first solution may comprise a deprotection/deblocking reagent. In other cases, the first solution is comprises an activated monomer (e.g. phosphoramidite or Fmoc- or Boc-protected amino acid along with coupling reagent). After delivery of the first solution, a subset or all of the channels/reaction vessels of the reaction plate can be washed with a wash fluid (e.g. in the case of oligonucleotide synthesis acetonitrile, in the case of peptide synthesis DMF). After washing, a subset or all of the channels/reaction vessels of the reaction plate can be flushed with a dry inert gas to fully displace all liquid within the channels/reaction vessels of the reaction plate. After flushing, the synthesis can be terminated or a new round of monomer addition may be initiated by delivery of new deprotection solution from the reagent delivery system, thus displacing all gas within the solid phase after flushing. Thus, since any subset of the channels/reaction vessels of the reaction plate can be selected for reagent delivery/washing/flushing, the channels/reaction vessels of the reaction plate (as well as the SSM and nascent polymer contained therein) are individually actuatable, and can be used to synthesize a different or unique biopolymer in each of the channels/reaction vessels of the reaction plate.

In some embodiments, the drain system 318 is configured to supply variable backpressure opposing the flow from the wash system 390/reagent control system 310 to allow for agitation and/or pneumatic displacement of reagent or wash solution within the channels/reaction vessels of the reaction plate. Backpressure from the drain system 318 allows for agitation/mixing of reagents saturating the SSM within the channels/reaction vessels 110 by exploiting a pressure differential between it and the reagent control system. Specifically, this agitation can be accomplished via alternating cycles of: a) providing positive flow or inert gas pressure from the wash system 390 with the drain system 318 open to displace solution within the channels/reaction vessels of the reaction plate in a first direction; and b) providing backpressure via the drain system 318 and negative pressure via the reagent control system 310 to displace solution within the channels/reaction vessels of the reaction plate in a second direction. These alternating cycles serve to alternate the direction of flow through the channels/reaction vessels of the reaction plate, and can be repeated multiple times (in various embodiments, at least two, at least three, at least four, or at least five times). Because variable negative/positive pressure at each channel can be provided via the reagent control system 310, agitation can be accomplished at one, a subset, or all channels/reaction vessels of the reaction plate. Such agitation can be useful for mixing reagents/solvents with the SSM during deprotection, coupling, and washing steps, or for providing a saturating excess of reagent during the coupling step (in various embodiments, this allows for e.g. between 1.3-fold and 20-fold, 5-fold and 15 fold, or 5-fold and 10-fold excess activated monomer relative to the sites of elongation on the solid phase medium to be provided). Moreover, this method of agitation allows for agitation without exposure of the SSM or any of the reagents to the ambient environment. This pressure-driven pneumatic agitation method also allows for several independent agitation parameters to be varied: the stroke (e.g. volume of wash or reagent liquid drawn through the reaction vessels and the SSM therein), the speed (e.g. the flow rate of wash or reagent liquid through the reaction vessels and the SSM therein), and the frequency (e.g. the time in between reversals of the direction of flow of the wash or reagent liquid drawn through the reaction vessels).

IV. Reagent Supply System

The reagent supply system 316 is configured to supply all of the necessary reagents and reagent mixes for the individual synthetic steps of the synthesizer, in such a way that all the reagents/reagent reservoirs are isolated from the external/ambient environment. In some embodiments, all the reagents are supplied via reagent bottles pressurized by an inert gas source. The reagents typically involve at least a reaction solvent (e.g. in the case of nucleotides, anhydrous acetonitrile), a plurality of monomers (e.g. in the case of nucleotides phosphoramidites), and an activation reagent (e.g. in the case of nucleotides, a tetrazole). For any polymer, the individual reagents needed for any given elongation step (e.g. coupling, washing, oxidation) reagents are typically the same with just the monomer solution changing. Accordingly, the monomers may be supplied by a first plurality of inert-gas pressurized reagent bottles each with an influent line connecting them to a first common multi-way selection valve having a first outlet line. The first plurality of inert-gas pressurized reagent bottles may also include a bottle of the reaction solvent (e.g. acetonitrile) so that the system can be cleaned between delivery of different monomers. Mixing of the monomers with activator may be accomplished by connecting the first outlet line and a second outlet line being fed from a pressurized bottle of activator solution to separate pump systems connected to a common mixer with an outlet valve which feeds the lower manifold 314. In some embodiments, other solutions (deblocking, oxidation, capping) may be fed via a second multi-way selection valve and/or pump system which similarly feeds the lower manifold 314. The reagent supply system 316 may additionally comprise a pressure selector, which in some cases can serve to modulate pump flow rate, to maintain integrity of the solid phase, or to prevent pressure deviations which may compromise the closed architecture of the system.

In any event, the reagent supply system is configured to supply monomers, activation solution, coupling solution, and any other synthetic step-required reagent both separately and in combination with reaction solvent. In the case of solid-phase DNA synthesis, the relevant reagents may include 2'-protected phosphoramidites such as dT-CE Phosphoramidite (5'-Dimethoxytrityl-2'-deoxythymidine, 3'-[(2-cyanoethyl)-(N,N-diisopropyl)]-phosphoramidite), iBu-dG-CE Phosphoramidite (5'-(4,4'-Dimethoxytrityl)-N-isobutyryl-2'-deoxyguanosine, 3'-[(2-cyanoethyl)-N,N-diisopropyl]-phosphoramidite), Bz-dA-CE Phosphoramidite (5'-(4,4'-Dimethoxytrityl)-N-benzoyl-2'-deoxyadenosine, 3'-[(2-cyanoethyl)-(N,N-diisopropyl)]-phosphoramidite), Bz-dC-CE Phosphoramidite (5'-(4,4'-Dimethoxytrityl)-N-benzoyl-2'-deoxycytidine, 3'-[(2-cyanoethyl)-(N,N-diisopropyl)]-phosphoramidite), activator (e.g. tetrazole), solvent (e.g. acetonitrile), deblocking solution (e.g. 3% TCA in dichloromethane), oxidizing solution (e.g. $I_2$ in THF/pyridine), and capping solution (e.g. acetic anhydride/pyridine/THF). In the case of solid phase RNA synthesis, the relevant reagents may include DMT-2'O-TC-rC(ac) Phosphoramidite (N4-Acetyl-O5'-(4,4'-dimethoxytrityl)-O2'-(1,1-dioxothiomorpholine-4-thiocarbonyl)cytidine O3'-(O-(2-cyanoethyl)-N,N-diisopropylphosphoramidite)), DMT-2'O-TC-rU Phosphoramidite (O5'-(4,4'-dimethoxytrityl)-O2'-(1,1-dioxothiomorpholine-4-thiocarbonyl)uridine O3'-(O-(2-cyanoethyl)-N,N-diisopropylphosphoramidite)), DMT-2'O-TC-rG(ib) Phosphoramidite (N2-Isobutyryl-O5'-(4,4'-dimethoxytrityl)-O2'-(1,1-dioxothiomorpholine-4-thiocarbonyl)guanosine O3'-(O-(2-cyanoethyl)-N,N-diisopropylphosphoramidite)), DMT-2'O-TC-rA(bz) Phosphoramidite (N6-Benzoyl-O5'-(4,4'-dimethoxytrityl)-O2'-(1,1-dioxothiomorpholine-4-thiocarbonyl)adenosine O3'-(O-(2-cyanoethyl)-N,N-diisopropylphosphoramidite)), activator (e.g. tetrazole), solvent (e.g. acetonitrile), deblocking solution (e.g. 3% TCA in dichloromethane), oxidizing solution (e.g. $I_2$ in THF/pyridine), and capping solution (e.g. acetic anhydride/pyridine/THF). For solid phase peptide synthesis, the reagents may include the 21 natural amino acids protected by Fmoc groups (e.g. Fmoc-Ala-OH, Fmoc-Gly-OH), activator solution (e.g. HBTU with DIEA), solvent (e.g. DMF and optionally DCM), and deblocking solution (e.g. piperidine in DMF).

V. Multi-Vessel Reaction Plate

FIGS. 1A through 1E show views of a reaction plate 100 (also known as a cartridge) for synthesizing oligonucleotides according to an embodiment of the present invention. FIG. 1A shows a side view of reaction plate 100. Reaction plate 100 has a top surface 102 (see FIG. 1B) and bottom surface 104 (see FIG. 1C). In some embodiments, a flange 106 is provided adjacent top surface 102. Additionally, in some embodiments, reaction plate 100 is keyed by the use of step 108 such that it is not symmetrical. This keying ensures that the reaction plate, when mounted to an oligosynthesizer can only be mounted in one orientation. The reaction plate 100 contains and/or defines the plurality of reaction vessels, which are provided as cylindrical lumens (e.g. channels with open tops and bottoms) within the reaction plate. In some embodiments, reaction plate 100 includes at least 2, at least 64, at least 96, at least 128, at least 254, at least 384, at least 512, at least 1056, at least 1536, at least 2112, or at least 4224 vessels 110 in the form of cylindrical lumens (e.g. channels with open tops and bottoms) which pass from top surface 102 to the bottom surface 104. In some embodiments, reaction plate 100 includes 64, 96, 128, 254, 384, 512, 1056, 1536, 2112, 4224 vessels 110 in the form of cylindrical lumens which pass from top surface 102 to the bottom surface 104. Such a design allows for the synthesis of at least 2, at least 64, at least 96, at least 128, at least 254, at least 384, at least 512, at least 1056, at least 1536, at least 2112, or at least 4224 polymers in parallel using the automated system described herein.

The body of reaction plate 100 is made of a non-porous solid material suitable for forming reaction vessels. Suitable materials include plastics, glass, metals etc. In preferred embodiments the non-porous solid material is thermally conductive such that heating or cooling may be applied to the reaction vessels through the reaction plate. For example, in a preferred embodiment, reaction plate 100 is machined from a single block of stainless steel. Stainless steel is thermally conductive such that it enables temperature regulation of all reaction vessels in the reaction plate by means of conduction through the reaction plate. Additionally, the reaction plate 100, when made of stainless steel, can be readily cleaned and reused.

Reaction plate 100 is designed for high-density synthesis of polymers. Different configurations of reaction plates can be used, however, in preferred embodiment the reaction vessels have a spacing compatible with standard (e.g. 96-, 384-, 1536-well) microplates to facilitate eluting completed polymers from the reaction plate into the standard microplates for subsequent purification and processing. In some embodiments, the lumens forming the reaction vessels pass through the full height of the reaction plate. In some embodiments, the reaction plate is approximately three inches wide, one and half inches tall, and less than a half an inch thick. In some embodiments, the full height of the reaction plate is one and a half inches. In some embodiments the reaction vessels are spaced at approximately 0.09 inches center-to-center and have a diameter of less than 0.09 inches.

Figure 1B:
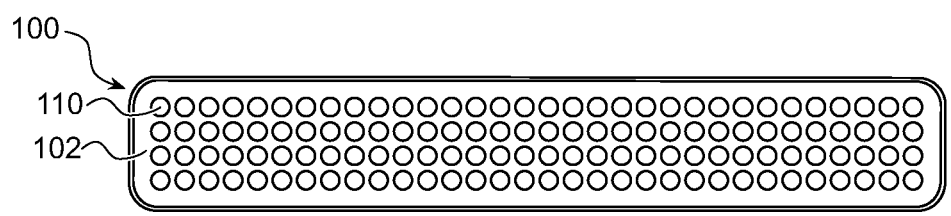
Figure 1C:
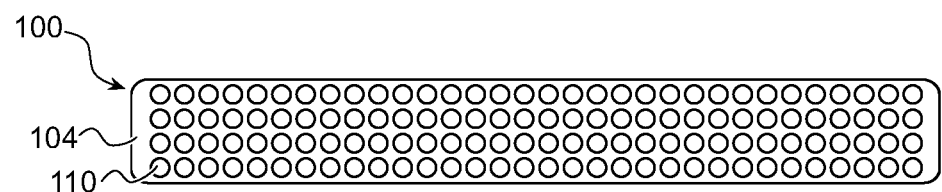

FIG. 1B and FIG. 1C show one embodiment of a reaction plate, wherein the plate is configured for 128 channels. On the top surface 102 of the reaction plate 100, the 128 reaction vessels 110 are shown arranged in four lines of 32 reaction vessels. The reaction vessels are packed at more than seventy reaction vessels per square inch of surface. The bottom surface 106 of the reaction plate 100 is shown in FIG. 1C, likewise with 128 reaction vessels 110. Both top surface 102 and bottom surface 104 are machined flat such that they form a seal when clamped into the oligonucleotide synthesizer.

Figure 1D:
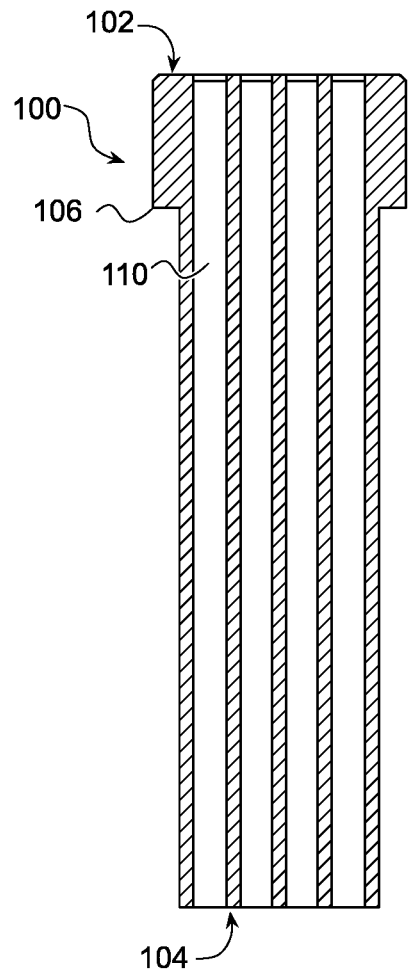
FIGS. 1D and 1E show sectional views of the reaction plate of FIGS. 1A, 1B and 1C.

FIG. 1D shows a sectional view through one embodiment of the reaction plate 100. FIG. 1D better illustrates flange 106 adjacent top surface 102 of reaction plate 100. As shown in FIG. 1D the section passes through four reaction vessels 110 in the form of lumens which pass from top surface 102 to bottom surface 104 of reaction plate 100. Although the lumens shown in FIG. 1D are cylindrical, lumens of different shapes may be used.

Figure 1E:
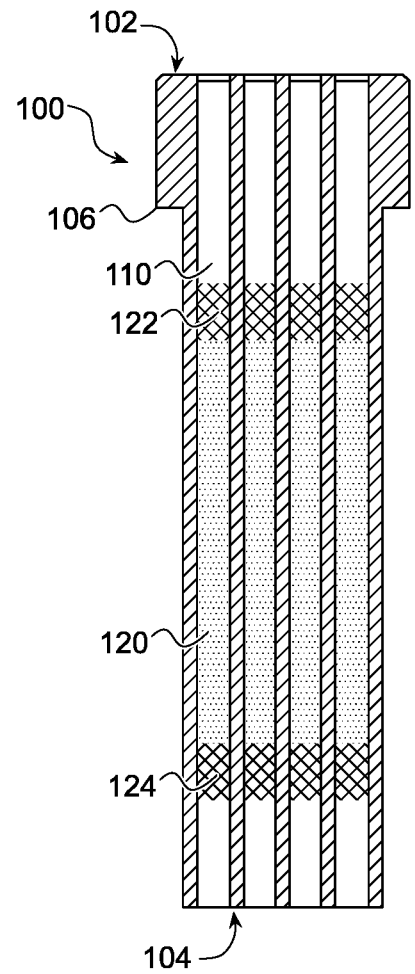

FIG. 1E shows a section view through the reaction plate 100 when prepared for synthesis of polymers. As described automated polymer synthesis methods typically employ a solid support media (SSM), such as polystyrene beads or controlled pore glass, to which starting monomers are covalently bound and then grown by repeating a cycle of monomer-addition reaction steps. The SSM allows the reagents used during a reaction step to be easily rinsed from the oligonucleotides to prepare for each subsequent reaction step. As shown in FIG. 1E, a column comprising a porous SSM 120 is packed into all of the reaction vessels 110. The SSM is held in place by first and second porous surfaces (e.g. frits, or filters that permit reagent solutions and solvents to pass through freely)) 122 and 124 at the top and bottom of each column. Frits 122 and 124 are polyethylene frits. In alternative embodiments, glass frits may be utilized. The SSM and frits are sufficiently porous to allow reagents to pass through the reaction vessels during oligonucleotide synthesis under the control of the synthesizer and/or the computer system attached thereto. In some embodiments, the two frits (top and bottom) separate a reaction volume that may be between 15 and 25, 15 and 50, 15 and 100, 15 and 200, or 15 and 300 microliters. In some embodiments, the two frits separate a reaction volume of about 15, 25, 50, 75, 100, 150, 200, 250, or 300 microliters. In some embodiments, the two frits separate a reaction volume of less than about 25, 50, 75, 100, 150, 200, 250, or 300 microliters.

In a preferred embodiment the SSM is controlled pore glass (CPG). In some embodiments, the SSM is polystyrene. In some embodiments the beads have a loading capability of from about 100 µmol per gram of bead to about 350 µmol per gram of beads. In some embodiments, the beads have an average particle size of from about 5 µm to about 500 µm, from about 10 µm to about 300 µm, from about 20 µm to about 100 nm, or about 50 µm to about 200 µm in diameter. In some embodiments, the beads have a specific surface area of from about 5 to about 200 $m^2/g$, from about 10 to about 100 $m^2/g$, or from about 20 to about 70 $m^2/g$. In a particular embodiment, the SSM is packed in to the reaction plate 100 after synthesis of common polymers on the SSM in a different synthesizer. Moreover, as described below, a sample of the polymers may be analyzed such that each reaction vessel 110 is loaded with a quantified amount of the common polymers (e.g. oligonucleotides, peptides) on the SSM.

In some embodiments, the multi-vessel/channel reaction plate 100 is temperature-controlled and/or can supply a temperature that differs from ambient temperature. In some embodiments, this is accomplished by a heater actuator 356 and a temperature control system 354 which are both in thermal communication with the reaction plate 100. In various embodiments, the multi-channel reaction plate 100 is configured to maintain a constant temperature of about 35° C., about 40° C., about 50° C., about 55° C., about 60° C., about 65° C., about 70° C., about 75° C., or about 80° C. In some embodiments, the multi-channel reaction plate 100 is configured to maintain a temperature between about 30° C. and 80° C., about 35° C. and 65° C., about 35° C. and about 50° C., or about 35° C. and about 45° C. In some embodiments, the reaction plate (e.g. under control of a computer system) may be configured to provide different temperatures for different synthetic steps (e.g. deblocking vs coupling vs capping vs oxidation). Thus, by the use of a temperature-controlled reaction plate, the automated synthesis system described herein can increase the reaction rate (e.g. for deprotection, coupling, oxidation, capping) of synthetic steps within each of the channels/reaction vessels of the reaction plate.

VI. Multi-Stage Method for Synthesizing Polymers

Different polymer synthesizer systems have different advantages and disadvantages during operation. In the case of oligonucleotide synthesizers, for example, large single column oligosynthesizer systems are available that can synthesize oligonucleotides on solid supports packed into columns having from 5 cm to 1 m internal diameter. Depending upon the solid support loading, packed bed height, and column diameter, these systems are capable of producing from 3 mmol to 2.5 mol of a single oligonucleotide at a time. Such systems typically allow for a wide variety of reagent options. However, because the system has a single synthesis column, only a single oligonucleotide sequence can be made at a time. In comparison, multichannel polymer systems are available which synthesize multiple different polymers at a time in parallel (for example 128 different oligonucleotides, peptides, etc). Such systems typically use low volume reaction plates in the format of microplates and are capable of making from 2 to 20 nmol of e.g. oligonucleotide at a time. Synthesis times are typically longer per monomer (nucleotide) in such systems because the activated monomer (phosphoramidite) reagents are added to the reaction vessels by delivery heads which move from vessel to vessel to add the desired reactant. Moreover the low volume of reagents and open reaction vessels (among other factors) leads to more process variability than is found in large single column (oligo)synthesizers. See, e.g. the Multisyn oligonucleotide synthesizer described by Cheng et al., "High throughput parallel synthesis of oligonucleotides with 1536 channel synthesizer" Nucleic Acids Research, 2002, Vol. 30 No. 18 e93 (Oxford University Press 2002) which is incorporated herein by reference.

A multi-stage method for synthesizing polymers makes use of different polymer systems to perform different stages in the synthesis of multiple polymers. In a first example, a large number of different polymers are desired but they all have the same initial sequence of monomers. In a first stage of the multi-stage synthesis method, a large amount of a first portion of the polymer (e.g. a 5-mer oligonucleotide or oligopeptide) can be synthesized in the high volume column of large single column synthesizer. The solid support medium bearing the first portion of the polymer can then be transferred to multiple small reaction vessels of a multichannel synthesizer. In a second stage of the multi-stage synthesis method, the different terminal portions of the polymers (e.g. the last 3 nucleotides or amino acids of an 8-mer oligonucleotide or oligopeptide) are synthesized.

In a second example, a large number of different polymers are desired but they all have the same terminal monomer or group of monomers (e.g. different last amino acid or last 3 amino acids of a polypeptide). In a first stage of the multi-stage synthesis method, a multichannel synthesizer is used to synthesize different polymers in each vessel of a multi-vessel reaction plate. The multi-vessel reaction plate can then be transferred to a second synthesizer which is designed to apply the same reagents to all reaction vessels in parallel. In a second stage of the multi-stage synthesis method, the different terminal portions of the polymers are synthesized in parallel on the second synthesizer.

In a third example, different polymers are desired where certain residues of the polymer are modified or labelled (e.g. the last 3 nucleotides of an 8-mer oligo are to be dye-labeled). In a first stage of the multi-stage synthesis method, a multichannel synthesizer is used to synthesize different polymers in each vessel of a multi-vessel reaction plate. The multichannel synthesizer provides the non-modified/non-labelled activated monomers (e.g. phosphoramidite reagents). The multi-vessel reactions plate can then be transferred to a second synthesizer which can provide the modified/labelled activated monomers (e.g. phosphoramidite reagents containing the dye). In a second stage of the multi-stage synthesis method, the different terminal portions of the polymers are synthesized in parallel on the second synthesizer using the modified/labelled activated monomers (e.g. phosphoramidites).

The multi-stage synthesis method need not be limited to two stages. In alternative methods three or more synthesis stages are used. The solid support material and/or multi-channel reaction vessel containing the solid support material is transferred from one synthesizer to another synthesizer between each stage. The different synthesizers have different synthesis capabilities or reagent availabilities necessary for each stage.

Figure 2A:
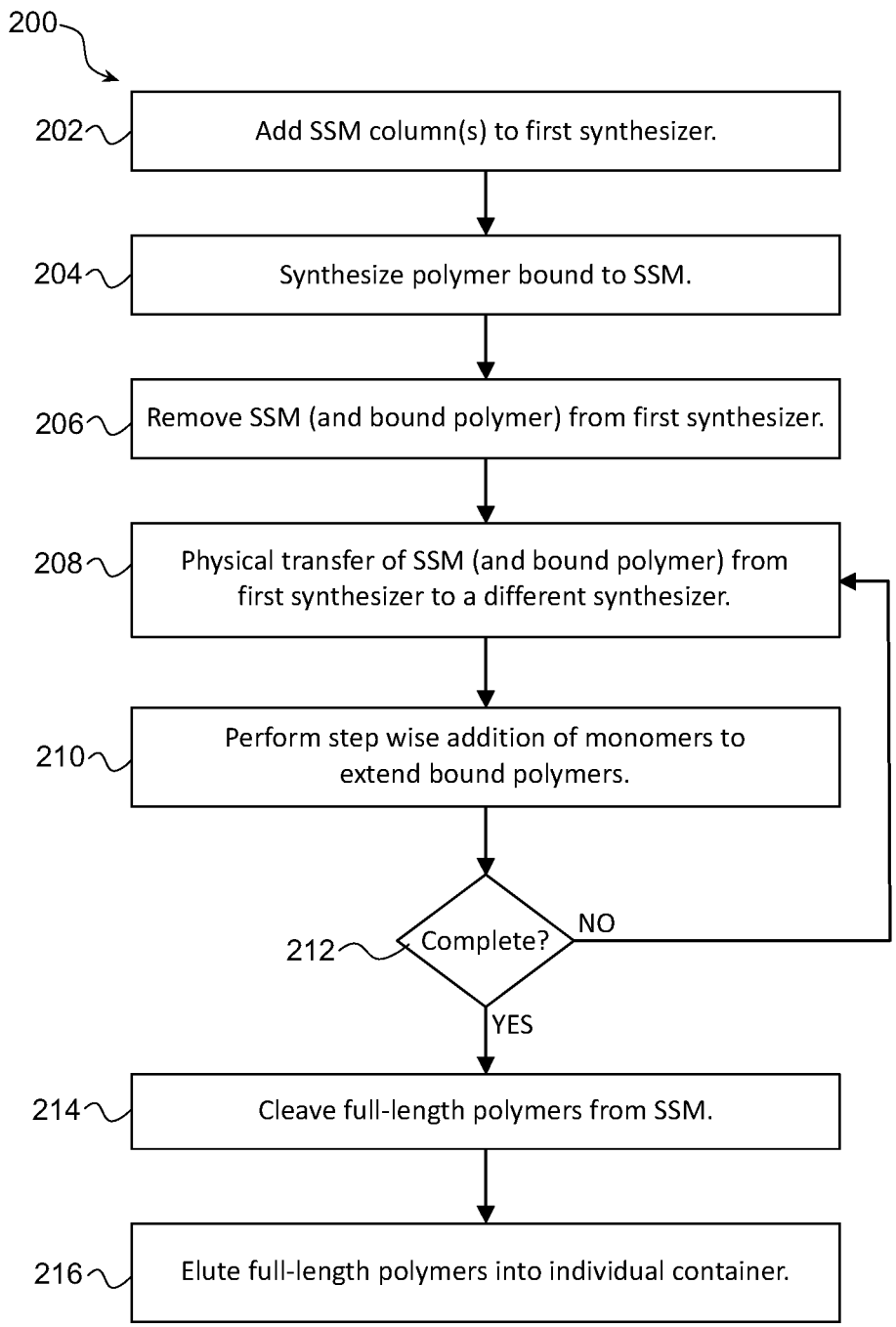
FIG. 2A shows an improved method for synthesizing oligonucleotides.

FIG. 2A shows a general embodiment of a multi-stage synthesis method 200. As shown in FIG. 2A, two or more different synthesizers may be utilized for the synthesis. In step 202 one or more columns of SSM are added to a first synthesizer. At step 204, the first synthesizer is operated to synthesize polymers on the columns of SSM. At step 206 the SSM and bound polymer is removed from the first synthesizer. At step 208 the SSM and bound polymer are physically transferred from the first synthesizer to a different synthesizer. During the transfer step, the SSM may optionally be moved from one reaction vessel to another or divided among different reaction vessel. During the transfer step, quantitative analysis of a sample of the partial polymers may optionally be performed. The synthesizer may be different from the first synthesizer in terms of number of channels and/or number of reagents, and/or types of reagents and/or other synthesis features. At step 201 the synthesizer is operated to perform stepwise addition of further monomers to the polymers previously created. At step 212, if the synthesis is not yet complete, the method repeats steps 208 and 210 with another different synthesizer (or return to the first synthesizer). At step 212, if the synthesis is complete, the method proceeds to cleave the full-length polymers from the SSM at step 214 and elute the full-length polymers from the SSM at step 216.

In some situations it is desirable to synthesize long chain oligonucleotides of the order of 100 nucleotides in length. A multi-vessel reaction plate can be used for stepwise synthesis of multiple different oligonucleotides simultaneously.

However in some cases it is desirable to synthesize multiple different oligonucleotides which have a common header sequence. For example, all of the desired oligonucleotides may have the identical sequence in a first region of the oligonucleotide nucleotides and then different sequences for the remaining nucleotides. While it is possible to synthesize such molecules entirely within a multi-vessel reaction plate, improved efficiencies may be obtained using the method illustrated in FIG. 2B. This same method can be used to synthesize other polymers (e.g. amino acids, oligosaccharides), wherein the first group of residues is to be identical among a group.

Figure 2B:
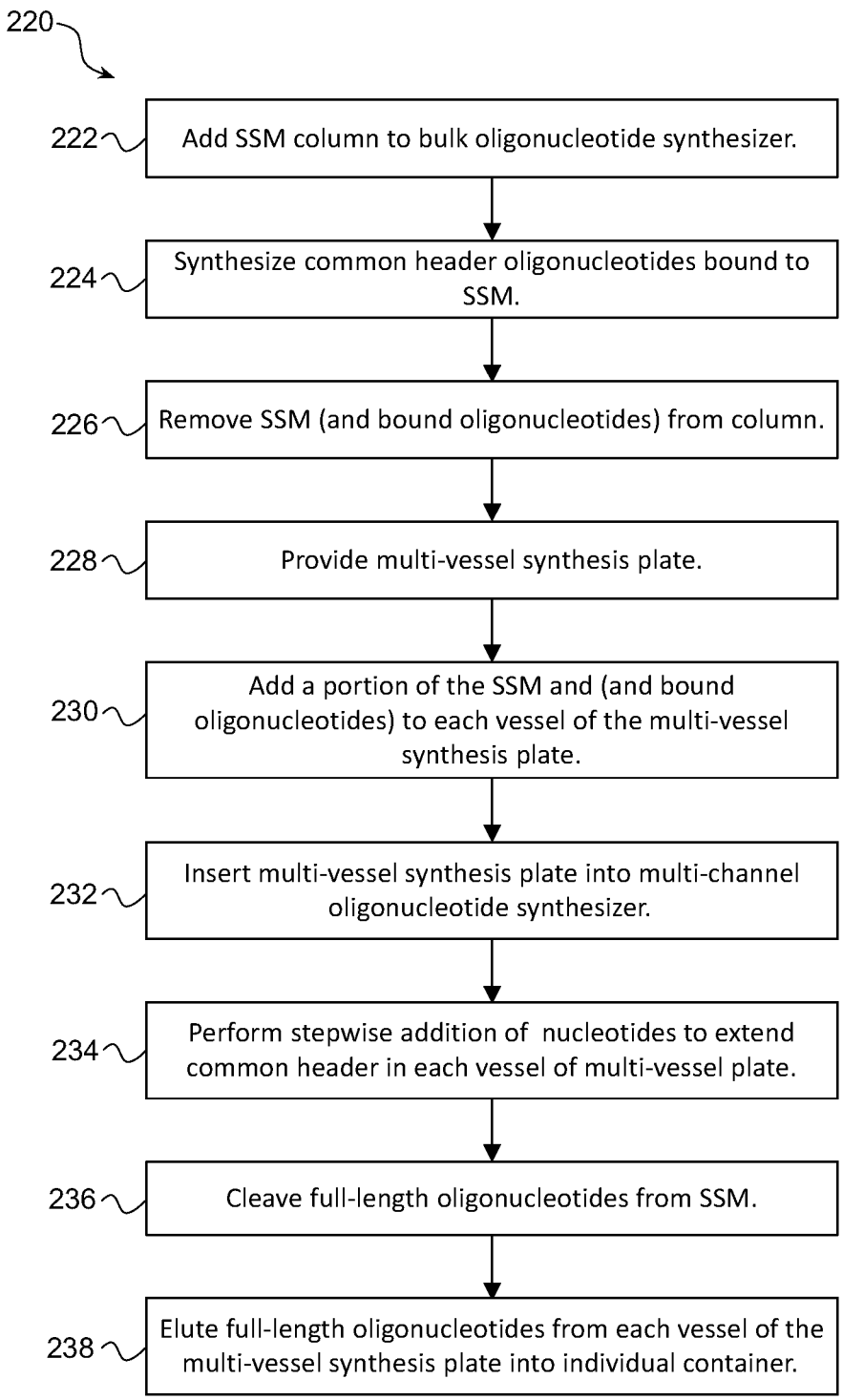
FIG. 2B shows a particular embodiment of the improved method for synthesizing oligonucleotides.

As shown in FIG. 2B, two different oligonucleotide synthesizers may be utilized for the synthesis. In a first synthesis stage, a single column oligonucleotide synthesizer is used to synthesize the common header portion of the desired oligonucleotides (or polymer). A single reaction vessel containing a column of SSM is used to form the common header portion of the oligonucleotides bound to the SSM. The use of the large column is efficient in terms of time and reagents than preparing this portion of the oligonucleotides in multiple separate reaction vessels. After the first synthesis stage, the SSM with the partial oligonucleotides (or partial polymer) attached is removed from the reaction vessel of the single column synthesizer. The SSM and partial oligonucleotides (or polymer) are then loaded into a multi-vessel reaction plate (e.g. the reaction plate of FIGS. 1A to 1E, or a conventional microplate). In a second synthesis stage, independent stepwise synthesis or the remaining portion of the oligonucleotides (or polymer) is performed in each vessel of the multi-vessel reaction plate.

Referring again to FIG. 2B, the method 220 begins at step 222 with the loading of a derivatized SSM column to a single column synthesizer. At step 224, the single column synthesizer is operated to synthesize the common header portion of the polymers (e.g. first 3 nucleotides). The monomers are added sequentially using conventional deprotection/coupling methods until the common header portion of the polymers has been synthesized. The partial polymers are covalently bonded to the SSM in the single reaction vessel of the single column synthesizer.

At step 226, the SSM with covalently bound partial polymers is removed from the single column synthesizer. At step 228 a multi-vessel reaction plate is provided. At step 230 a portion of the SSM with covalently bound partial polymers from the single column synthesizer is loaded into each vessel of a multi-vessel reaction plate. The partial polymers may be prepared in large volume and stored for some time prior to the second stage. Additionally, depending on the size of the single column oligosynthesizer, the amount of partial polymers prepared may be sufficient for use in several or many multi-vessel reaction plates.

During the transfer step, partial polymers may be cleaved from a sample of the solid support material. The sample of partial polymers may be analyzed using HPLC or mass spectrometry to determine the quantity of reactive partial polymers present in the sample. After the number of reactive partial oligonucleotides have been quantified, this information can be used to determine how much of the solid support material should be loaded in the multi-vessel reaction plate in order to allow for synthesis of the desired quantities of the full-length polymers. Quantification of the partial polymers during the transfer step allows for quality control, as well as reagent savings. Moreover, accurate quantification of the partial polymers during the transfer step allows the reagent quantities in the second synthesis stage to be better matched to the number of available reaction sites—typically an excess of activated monomer (e.g. phosphoramidite) reagents is used to ensure all available reactive sites are utilized—where the number of sites has been quantified, the amount of excess reagent wasted can be minimized.

At step 232 the second synthesis stage commences with the multi-vessel reaction plate inserted into a multi-channel polymer synthesizer. The multi-channel synthesizer is capable of providing different reagents to each of the vessel in the multi-vessel reaction plate. Accordingly, the multi-channel synthesizer can perform stepwise synthesis of different terminal residues onto the common header polymer. At step 234 stepwise addition of different monomers is performed with different residue sequences being added to the common header portion in different vessels of the multi-vessel reaction plate. At step 236, upon completion of the different polymers, a cleavage step is performed to release the polymers from the SSM. Each vessel of the multi-vessel reaction plate is then eluted into an individual container or well at step 238.

The two stage synthesis method illustrated in FIG. 2B has several advantages compared to single stage synthesis. In general terms the two stage synthesis method makes use of the different advantages and properties of the two synthesizers used in the method. In the first stage, better quality of the header portion of the polymers can be achieved using the closed loop chemistry control available in the single column synthesizer. Quality and quantity of polymers can also be assessed by sampling during transfer prior to the second stage. The first stage can be completed ahead of time thereby reducing the time for delivering custom polymers by a factor of five (assuming a polymer with 80 residues in the first stage and 20 residues in the second stage). Moreover throughput of the multi-channel synthesizer (e.g. number of polymers or oligonucleotides per day) can be increased by a factor of five because 80 percent of the synthesis workload for each polymer is performed on the single column synthesizer.

In a particular embodiment, the method of FIG. 2B is utilized in the manufacture of synthetic single molecule guide RNA (gRNA) for use in CRISPR. In gRNA molecules, the header polymer (oligonucleotide) is approximately eighty residues (nucleotides) in length. This portion of the RNA molecule interacts with the Cas9 protein to form the CRISPR Cas9 complex. The sequence of residues (nucleotides) in this portion of the guide RNA thus does not change from gRNA to gRNA. The remaining approximately twenty nucleotides of the gRNA interact with the target DNA molecule. The sequence of this portion of the guide RNA is therefore selected such that the CRISPR/Cas9 complex targets and binds to a selected sequence on the target DNA molecule. The sequence of this portion of the RNA molecule thus varies dependent upon the selected sequence on the target DNA molecule to be targeted and needs to be customized for a particular application.

Accordingly the synthesis of CRISPR guide RNA molecules is an ideal application of the method of FIG. 2B. The first portion of the gRNA is synthesized bound to SSM in a single column synthesizer. Subsequently the SSM and covalently bound partial RNA molecules are removed from the synthesis vessel of the single column synthesizer. A sample of the partial RNA molecules may be cleaved and quantified. Subsequently measured amounts of SSM and covalently bound partial RNA molecules can be loaded into a multi-vessel reaction plate. The multi-vessel reaction plate is then transferred to a multi-channel oligo-nucleotide synthesizer which continues with stepwise addition of nucleotides in a selectable manner in the separate reaction vessels. In this way custom RNA sequences can be synthesized starting with the common header sequence already synthesized in an efficient manner to generate customized synthetic single-molecule guide RNA molecules in an efficient and expedient manner.

Figure 2C:
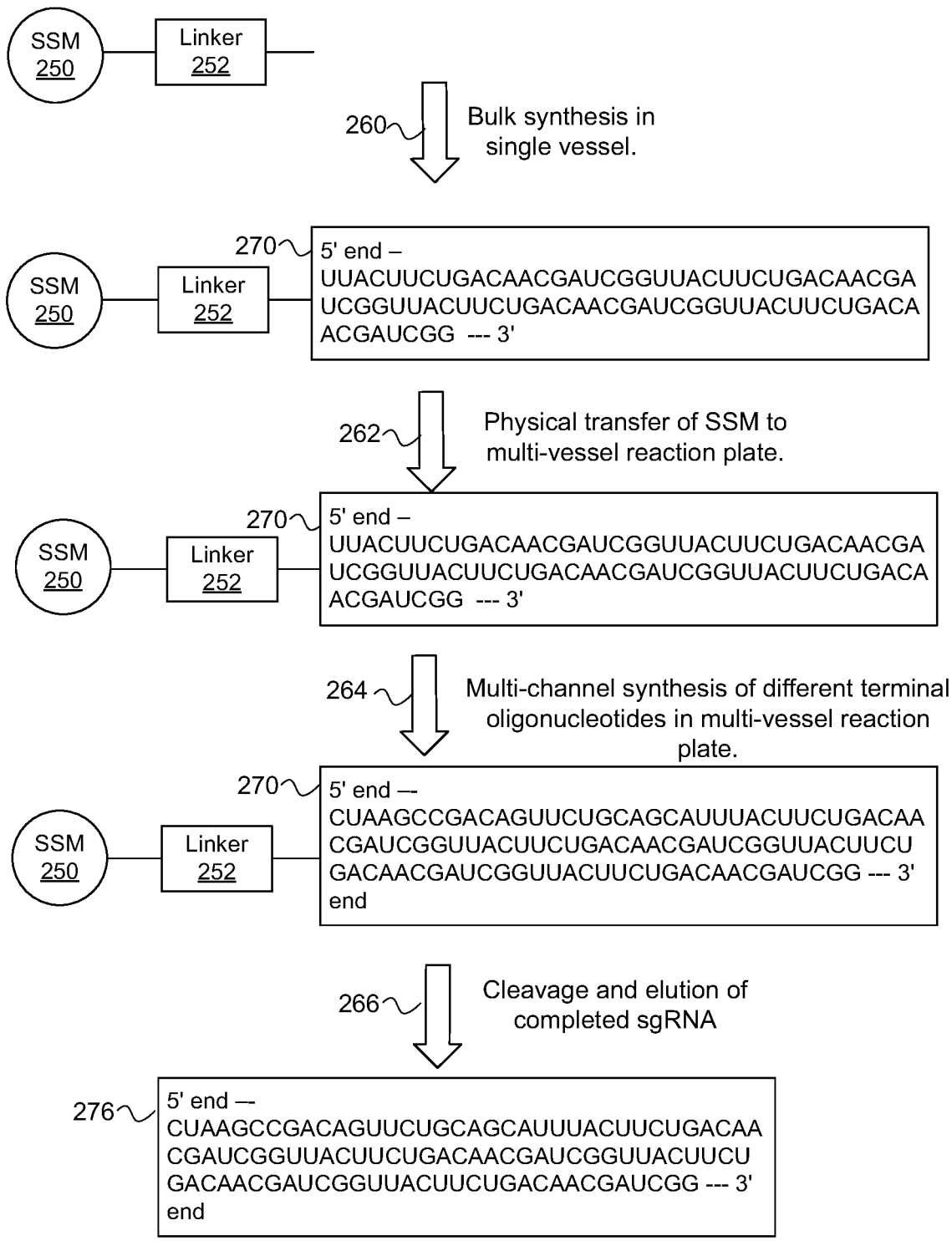
FIG. 2C shows a particular embodiment of the improved method for synthesizing oligonucleotides in the form of CRISPR guide RNA. Figure discloses SEQ ID NOS 2, 2, 3 and 3, respectively, in order of appearance.

This method is illustrated in FIG. 2C. As shown in FIG. 2C, SSM 250 derivatized by addition of a linker 252 is loaded into the reaction vessel of a single column oligonucleotide synthesizer. In a first RNA synthesis stage 260, the single column oligonucleotide synthesizer is used to synthesize an 80-mer sequence 270 in which the 3' end is covalently bonded to the linker 252 and SSM 254. After completion of the 80 mer sequences, the SSM 250 and covalently bound 80 mer sequences 270 are physically transferred 262 to multiple separate reaction vessels for use in a multi-channel oligonucleotide synthesizer. As described above, the 80 mer sequences may be quantified prior to the transfer step such that only as much SSM is loaded into the multi-vessel reaction plate as is required for the desired quantity of gRNA to be synthesized. This yields a multi-vessel reaction plate such as shown for example in FIG. 1A-1E preloaded with SSM with known quantities of covalently bound 80 mer sequences. After transfer, in second synthesis stage 264, the multi-channel oligonucleotide synthesizer is used to synthesize multiple different 20 mer sequences of RNA starting from the 5' end of the 80 mer sequences previously created. These 20 mer sequences are specific to the DNA target site. The completed 100-mer sequence is thus completed on the SSM in the multi-channel synthesizer. Then at step 266, the completed gRNA molecules 276 are cleaved from the SSM by cleaving the linker 252 and eluting the oligonucleotide molecules into separate volumes.

The sequences shown in FIG. 2C are for illustrative purposes only. Different common header sequences and lengths and terminal sequences and lengths may be used depending on the application to which the RNA may be put. Moreover the same principles may be applied to biopolymer synthesis other than gRNA where different terminal sequences are added to common header sequences of e.g. DNA, RNA, and polypeptides.

VII. Multi-Channel Oligonucleotide Synthesizer

FIGS. 3A and 3B show views of a multi-channel synthesizer 300. FIG. 3A shows a block diagram of a system 300 for synthesizing polymers using the reaction plate 100 of FIGS. 1A to 1E. FIG. 3B shows a sectional view of the reaction plate 100 loaded into the multi-channel synthesizer 300.

Multi-channel synthesizer 300 comprises a plurality of channels, each of which allows for independent synthesis of a polymer by stepwise extension of the polymer (in the embodiment shown, the synthesizer contains 128 channels). In order to control polymer manufacture, the synthesizer independently controls which activated monomer (e.g. nucleotide phosphoramidite) reagents are added to each reaction vessel of the reaction plate 100. As shown in FIGS. 1A-1E, reaction plate 100 includes a plurality of separate reaction vessels such that a different polymer can be synthesized in each vessel of the reaction plate. In some embodiments, reaction plate 100 is scaled to include at least 128, at least 384, at least 1536, at least 3456, or at least 9600 reaction vessels. In some embodiments reaction plate 100 is scaled to include 128, 384, 1536, 3456, or 9600 reaction vessels. Thus although the embodiment shown has 128 vessels, the inventions described herein can be applied to reaction plates having thousands of reaction vessels.

Reaction plate 100 is mounted in synthesizer 300 by being clamped between upper manifold 312 and lower manifold 314. A clamp actuator 304 under control of computer control 302 moves upper manifold 312 towards lower manifold 314 after loading of reaction plate 100. The clamp actuator pushes the sealing surfaces of the reaction plate into contact with the mating surfaces of the upper and lower manifold forming a seal. Both upper manifold 312 and lower manifold 314 include on their surface a set of apertures which align with the vessels of reaction plate 100. When clamped in place, the surfaces of the manifolds create a seal which prevents leakage of reagents from between the manifolds and the reaction plates and also seals each reaction vessel from the adjacent reaction vessels thereby providing a plurality of closed reaction vessels. This sealing enables the supply system to control entry of reagents into the vessels and also prevents entry of contaminants (e.g. water molecules) during the monomer addition cycle in a manner that is superior to the open reagent delivery mechanisms of prior systems.

Lower manifold 341 also includes registration features 320 which engage the keying feature of reaction plate 100 to ensure that the reaction plate is loaded in the correct orientation. This prevents user error in loading the reaction plate 100 into synthesizer 300. Upper manifold 312 connects the vessels of reaction plate 100 to the reagent control system 310. Lower manifold 314 connects the vessels of reaction plate 100 to reagent supply system 316 and drain system 318.

FIG. 3B shows a sectional view of reaction plate 100 clamped between upper manifold 312 and lower manifold 314. As shown in FIG. 3B, lower manifold 314 includes a common interior lumen 340 with which all the reaction vessels 110 of the reaction plate 100 are in fluid communication. As shown in FIG. 3B upper manifold 312 includes a separate lumen 332 for each of the reaction vessels 110. Each separate lumen 332 connects each reaction vessel 332 to its own subsystem 330 on the reagent control system 310. The subsystems 330 (in one embodiment, 128 total) allow for individual control and selective delivery of reagent to the 128 reaction vessels 110 in reaction plate 100. The subsystems 330 can be selectively actuated under the control of computer control 302 to deliver reagents into reaction vessels 110 or purge reagents from reaction vessels 110 into lower manifold 314. For instance, with reference to FIG. 3D, in some embodiments, a reagent control system may comprise a pressure selector 394. The pressure selector 394 may be configured to alternatively (1) "pull" (exert negative pressure) to draw fluid into reaction vessels 110 and (2) "push" (exert positive pressure) to expel fluid from the reaction vessels 110. Valves (e.g., solenoid valves) 395 may be used to selectively draw and/or expel liquid into and from individual reaction vessels 110.

Thus, reagent control system 310 may be configured to allow for reagent delivery to a selected subset of the plurality of reaction vessels under computer control 302. The selected subset can include between one of and all of the reaction vessels simultaneously. Stated differently, in some embodiments, valves 395 may be under control of computer 302.

Referring again to FIG. 3A, selectable reagent supply 316 is configured to introduce reagents into lower manifold 314 under computer control 302. Selectable reagent supply 316 comprises a set of valves and pumps which can introduce one or more selected reagents or cleaning solvents into manifold 314. Selectable reagent supply 316 can be configured to provide standard phosphoramidite reagents as well as modified/labelled phosphoramidite reagents and acetonitrile (ACN) as specified by computer control 302. One reagent at a time is provided to lower manifold 314 with reagents cleaned and purged from lower manifold 314 between synthesis steps. Anhydrous ACN (e.g. for oligonucleotide synthesis) can be used for example as a cleaning/purging solvent between monomer-addition cycles. Anhydrous DMF (e.g. for peptide synthesis) can be used for example as a cleaning/purging solvent between monomer-addition cycles. Accordingly computer control system 302 can control which reagent is present in lower manifold 314 (by means of selectable reagent supply 316) at any point in a reaction process and also control which reaction vessels receive the reagent present in lower manifold (by means of reagent control system 310). Accordingly computer control system 302 can selectively deliver each of the reagents available from selectable reagent supply 316 to particular vessels of the reaction plate.

Drain system 318 is configured for drainage of reagents and/or cleaning solvents from the lower manifold 314 under control of computer control 302. Drain system 318 comprises a set of valves which can remove reagents or cleaning solvents from manifold 314 to either a common drain or separate drains for different reagents/solvents. The vacuum supply can also be used to apply negative pressure to the lower manifold 314 (e.g. in order to promote removal of reagents from the reaction plate 100) as well as positive pressure to the lower manifold 314 (e.g. to promote agitation/mixing of reagents or wash solutions with the solid phase in the channels/reaction vessels 110).

In use, reaction plate 100 is clamped into place between upper manifold 312 and lower manifold 314. Mating surfaces of upper manifold 312 and lower manifold 314 ensure sealing at the top surface 102 and bottom surface 104 of the reaction plate 100 each of the reaction vessels is sealed from each other. A computer control system 302 controls reagent control system 310, reagent supply system 316 and drain system 318 to cause manifold 314 to contain the appropriate reagent at a particular point in time. The computer control system then operates reagent control system 310 to deliver reagent to a selected subset of the plurality of reaction vessels wherein the selected subset can include between one of and all of the reaction vessels simultaneously. Computer control system 302 then controls reagent supply system 316 and drain system 318 to cause lower manifold 314 to be cleaned and then filled with the next required reagent. This process repeats stepwise until the desired reagents are added and removed stepwise to all the reaction vessels 110 as required for the particular synthesis.

The system of FIGS. 3A-3B is advantageous in that the reaction plate 100 is not required to be moved during use but instead remains clamped in place throughout the reaction. The reaction vessels are also sealed from the environment to prevent entry of contaminates. Moreover, the supply system for changing the reagents in manifold is relatively compact compared to prior systems. Accordingly, a system can provide a larger number of selectable reagents and/or be constructed in a more compact manner.

Furthermore, because upper manifold 312 and lower manifold 314 are sealed to reaction plate 100, the sealed system prevents exposure of the reagents to the atmosphere surrounding the reaction plate thereby reducing the risk of contamination and reducing the need for stringent control of the system atmosphere as compared to prior systems.

As described above multi-channel oligonucleotide synthesizer 300 is capable of synthesizing different oligonucleotides in each vessel of reaction plate 100. When conducting multiple different oligonucleotide synthesis reactions in parallel, it is important to maintain reactions efficiency and consistency between different reaction vessels and between different synthesis steps. One important factor in maintaining efficiency and consistency is ensuring that reactions take place at a consistent temperature from reaction to reaction and vessel to vessel.

As described above, reaction plate 110 is machined from a thermally conductive material such as stainless steel. This ensures that there is little variation in temperature between each of the reaction vessels 110. Additionally, to ensure proper temperature control during reactions, multi-channel oligonucleotide synthesizer 300 includes a temperature control system including a temperature control block 350 which is pushed into thermal contact with the rear side of reaction plate 100 by a heater actuator 356 after reaction plate has been clamped into the synthesizer 300. Temperature control block 350 includes heating and/or cooling elements 358 which can be used to maintain the temperature of block 350 and consequently reaction plate 100 at a set point desired for any given reaction. A temperature sensor 352, such as a thermocouple, monitors the temperature of reaction plate 100. A temperature control system 354 connected to temperature sensor 352 controls the heating or cooling of temperature control block 350 to increase or decrease the temperature of reaction plate 100 as required to achieve the desired set point temperature. The temperature control system is monitored and controlled by computer control 302.

Thus multi-channel oligonucleotide synthesizer 300 ensures consistency of temperature between reaction vessels and sequential reaction steps. In particular, the temperature control system can be used to heat reaction plate 100 to above ambient temperature. Heating of the reaction plate increases the rate of reaction for the various steps of the synthesis thereby reducing the amount of time required for the reactions to complete. Because synthesis of oligonucleotides requires a large number of sequential reaction steps, even a small reduction in time required for each step can significantly reduce the amount of time necessary for the full synthesis and thereby increase the throughput of the synthesizer in terms of number of different oligonucleotides synthesized per day. Accordingly use of a thermally conductive reaction plate in combination with temperature control system can dramatically increase system throughput for synthesis as compared to prior systems.

Figure 3C:
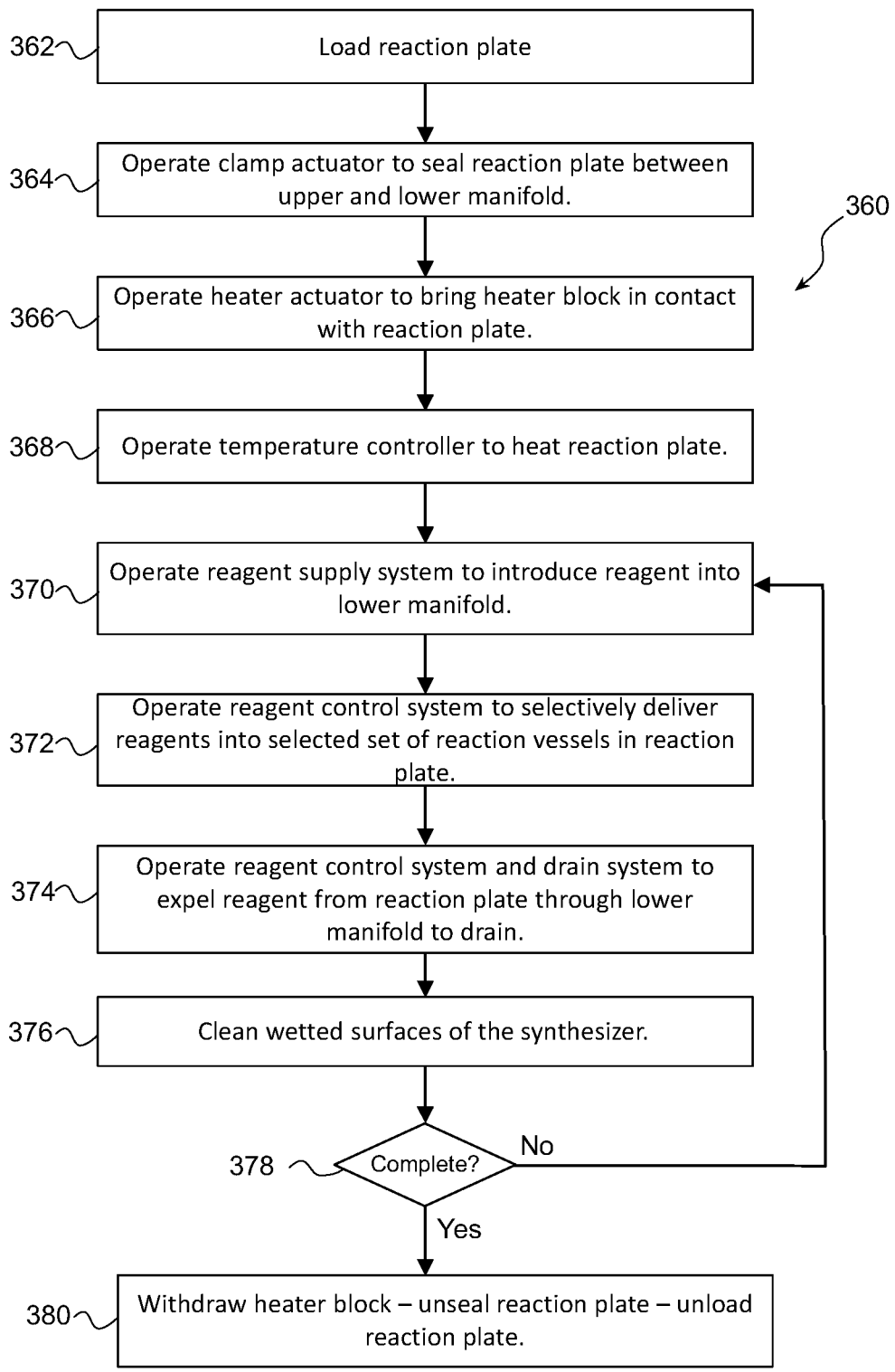
FIG. 3C shows a general method of operating the multi-channel oligonucleotide synthesizer of FIGS. 3A and 3B.
Figure 3D:
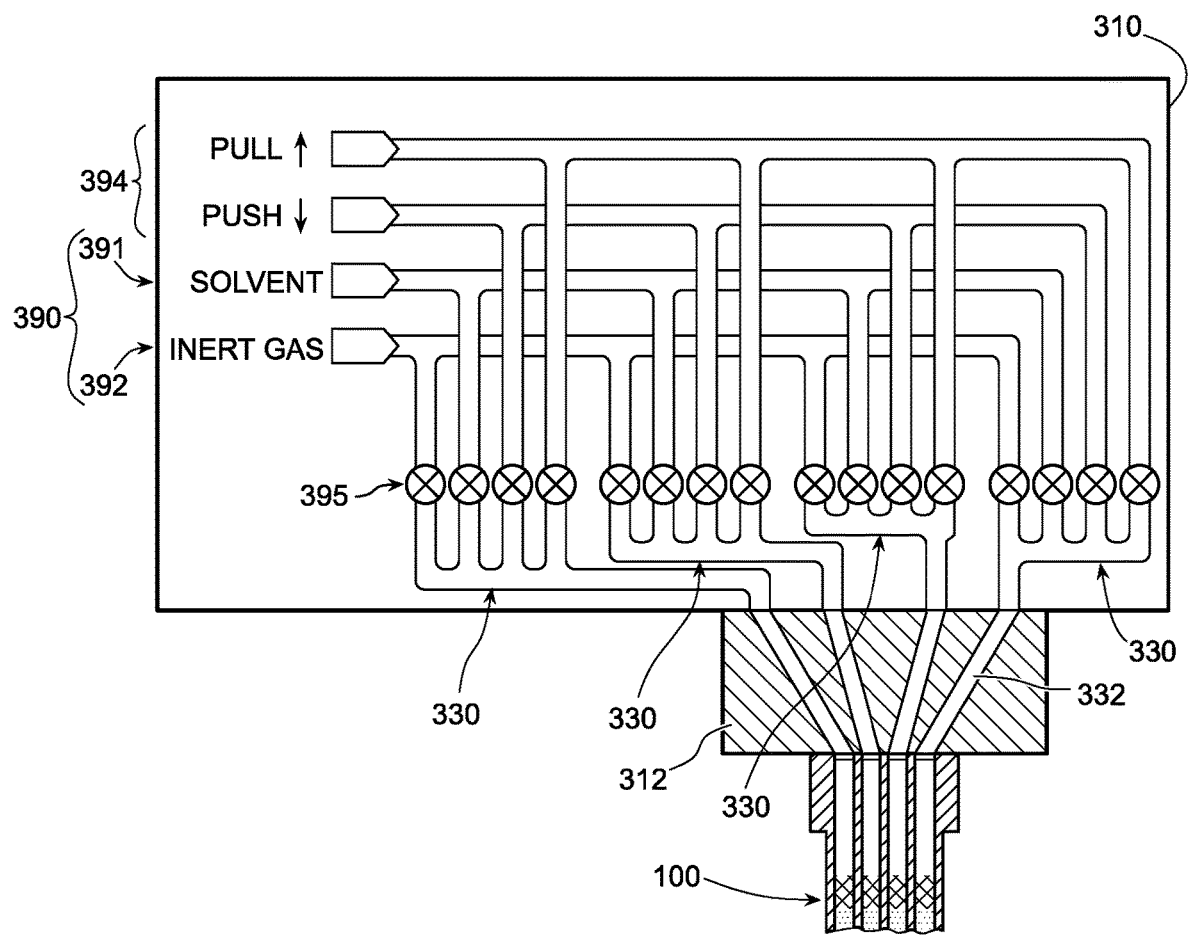
FIG. 3D shows one embodiment of a portion of an oligonucleotide synthesizer.

FIG. 3C shows a general method 360 of operating the multi-channel oligonucleotide synthesizer of FIGS. 3A and 3B. At step 362 the reaction plate is loaded into the synthesizer. At step 264 the clamp actuator is operated to clamp the reaction plate between the upper and lower manifolds forming seal between the manifolds and the reaction plate. At step 366, the heater actuator is operated to push the heater block into thermal contact with the reaction plate. At step 368 the temperature controller measures the temperature of the heater block and reaction block and applies heat and/or cooling to bring the reaction plate to the desired temperature (the temperature controller continues this process throughout the reaction cycle of steps 370-378).

The cycle for each reaction step is shown in general terms in steps 370 to 378. At step 370 the reagent supply system in cooperation with the drain system introduces a volume of a selected reagent into the lower manifold. At step 372, the reagent control system is operated to deliver the required reagent into a selected set of the reaction vessels of the reaction plate. After the reaction completes, at step 374 the reagent control system and drain system are operated to expel the reagent from the selected set of reaction vessels through the lower manifold and into the drain system for disposal or recycling. At step 376 a cleaning cycle is performed to flush the reagent from the reaction vessels and clean all wetted surfaces. At step 378, if the synthesis is not complete the method repeats steps 370 to 376 with the next reagent. At step 378, if the synthesis is complete, the method progresses to step 380 where the heater actuator withdraws the heater block and the clamp actuator unclamps the reaction plate thereby allowing the reaction plate to be unloaded from the synthesizer.

As described above, the monomer-addition cycle for synthesis of oligonucleotides comprises four basic steps: 1) a deblocking step using a deblocking reagent to remove a blocking group is removed from the 5' hydroxyl of the last-added nucleotide to produce an oligonucleotide with a free 5' hydroxyl group; 2) a chain elongation step in which a next appropriate phosphoramidite reagent is used to add one nucleotide subunit at the 5' end; 3) an oxidation step in which an oxidation reagent is used to oxidize the phosphite to produce a phosphate linkage; and 4) a capping step in which capping reagents are added to render any unreacted substrate hydroxyls or unreacted 5' hydroxyls of nascent oligonucleotides unreactive towards subsequent phosphoramidite additions. Thus each monomer addition cycle requires four steps and consequently four repetitions of steps 370 to 378 of FIG. 3C each with a different reagent (deblocking reagent, phosphoramidite reagent, oxidation reagent, and capping reagent).

The monomer addition cycle for peptides is similar, only omitting the capping and oxidation steps. Thus, the monomer addition cycle for peptides comprises two basic steps: a) a deblocking step using a deblocking reagent in which blocking group (e.g. Fmoc, Boc) is removed from the N-terminus of the last added nucleotide to produce a peptide with a free N-terminal amine group; and b) a chain elongation step in which a next appropriate activated blocked amino acid is used to add one amino acid subunit at the N-terminus. Thus each monomer addition cycle requires 2 steps and consequently four repetitions of steps 370 to 378 of FIG. 3C each with a different reagent (deblocking reagent, amino acid/coupling reagent).

At the end of the synthesis procedure, the completed polymer may be cleaved from the SSM, ideally after the SSM is dried of solvent under a flow of inert gas. This can be accomplished on or off the instrument. In some embodiments, the polymers are oligonucleotides, and the oligonucleotides are cleaved from the SSM via saturation of the SSM with concentrated aqueous ammonia at room temperature for a period of time (e.g. 30 minutes to 2 hours), followed by collection of the ammonia solution and evaporation or lyophilization of the ammonia solution. In some embodiments, the polymers are oligonucleotides, and the oligonucleotides are cleaved from the SSM via treatment with anhydrous ammonia gas at a temperature between ambient temperature and 90 degrees Celsius (e.g. between about 20 degrees and about 90 degrees Celsius) or between ambient temperature and 65 degrees Celsius (e.g. between about 20 degrees and about 65 degrees Celsius). Oligonucleotides cleaved via treatment with ammonia gas can then be collected from the SSM via elution from the SSM using water or an aqueous buffered solution. In some embodiments, the polymers are peptides, and the peptides are cleaved from the SSM via saturation of the SSM with a cleavage cocktail (e.g. TFA/$H_2O$/phenol/TIPS 8.5/0.5/0.5/0.5) and incubation at room temperature for a period of time (e.g. between 30 minutes and 3 hours). Peptides in the cleavage solution can be collected from the SSM by filtration, and the cleavage cocktail evaporated or lyophilized to yield the peptides.

VIII. Performance Parameters of Synthesizer System

In some embodiments, the present disclosure provides an (optionally automated and computer-controlled) multiplex solid-phase polymer synthesizer for the stepwise production of a polymer in improved yield to existing multiplex solid-phase synthesizer systems. In some embodiments, the synthesizer produces an oligonucleotide of at least 100 nucleotides in length with an average stepwise yield (ASWY) for the oligonucleotide greater than 98%, 98.5%, 99%, 99.2%, 99.5%, 99.6%, or 99.8%. In some embodiments, the synthesizer produces a DNA oligonucleotide of at least 100 nucleotides in length with an average stepwise yield (ASWY) for the oligonucleotide greater than 98%, 98.5%, 99%, 99.2%, 99.5%, 99.6%, or 99.8%. In some embodiments, the synthesizer produces an RNA oligonucleotide of at least 100 nucleotides in length with an average stepwise yield (ASWY) for the oligonucleotide greater than 98%, 98.5%, 99%, 99.2%, 99.5%, 99.6%, or 99.8%.

In some embodiments, the present disclosure provides an (optionally automated and computer-controlled) multiplex solid-phase polymer synthesizer for the stepwise production of a polymer with increased speed of parallel synthesis compared to existing multiplex solid-phase synthesizer systems. Because the system depends on simultaneous pneumatic delivery of reagents to multiple channels/reaction vessels rather than one-by-one delivery, the synthesizer system is able to provide faster parallel synthesis (whether measured in total time for synthesis of each complete polymer in the multiplex system, or the monomer addition cycle time for each polymer in the multiplex system) relative to an embodiment that uses an XY stage for delivery of reagent to a plurality of reaction vessels. Further, because of the faster parallel synthesis, the synthesizer system is able to provide process variability relative to an embodiment that uses an XY stage for delivery of reagent to a plurality of reaction vessels.

In some embodiments, the system is configured for oligonucleotide synthesis, in which case each monomer addition cycle comprises a deprotection step, four coupling steps (e.g., one for each phosphoramidite monomer), a capping step, and an oxidation step. In some cases, each coupling step (in which phosphoramidite plus activator is supplied through the lower manifold), is separated by solvent purge step (e.g. a flow of acetonitrile through the lower manifold to the drain/outlet) to purge residual monomer from the system. In some cases, each synthetic step (deprotection, coupling, capping, oxidation, etc), is separated by a solvent purge step. In this case of oligonucleotide synthesis, the monomer addition cycle may be less than about 60 minutes, less than about 45 minutes, less than about 30 minutes, less than about 15 minutes, less than about 10 minutes, or less than about 8 minutes. In some embodiments for oligonucleotide synthesis, just the coupling step is accomplished in less than about three minutes, less than about two minutes, less than about 1.5 minutes, less than about one minute, less than about 0.5 minutes, or less than about 0.25 minutes. As a result of these cycle times, the system (when configured for oligonucleotide synthesis) is able to supply a plurality of different 20-mer oligonucleotides (e.g. RNA or DNA oligonucleotides) in less than about 250, less than about 200, or less than about 160 minutes with a yield of at least 90%, at least 92%, or at least 95%.

In some embodiments, the system is configured for peptide synthesis, in which case each monomer addition cycle comprises a deprotection step, 21 coupling steps (e.g. one for each naturally-occurring amino acid), and a wash step. In some cases, each coupling step (in which activated amino acid is supplied through the lower manifold), is separated by solvent purge step (e.g. a flow of DMF through the lower manifold to the drain/outlet) to purge residual monomer from the system. In this case of peptide synthesis, the monomer addition cycle may be less than about 3 hours, less than about 2 hours, less than about 1 hour, or less than about 30 minutes. In some embodiments for peptide synthesis, just the coupling step is accomplished in less than about 2 hours, less than about 1 hour, less than about 45 minutes, less than about 30 minutes, less than about 15 minutes, or less than about 5 minutes.

EXAMPLES

Example 1

Multi-Column Synthesis of 96-Member Guide RNA Library with Identical Scaffold Sequence Using the methods and systems described herein, guide RNA (gRNA) constructs with identical ~80-mer scaffold sequences with 96 different 17-22 nucleotide protospacer domains (e.g. to target 128 distinct genomic regions) on their 5' end can be synthesized in a single batch via a two-phase process. In this process, the scaffold is first synthesized, and then the pool is split to further add the protospacer domains separately. Such guide RNAs can be used in transfection/microinjection experiments along with plasmid or mRNA-driven CRISPR enzyme constructs to introduce targeted genome insertions/deletions in eukaryotic or bacterial cells.

Alternatively, the gRNA constructs can be synthesized as DNA complementary to the desired scaffold+protospacer sequence and cloned into a vector with e.g. an SP6 RNA polymerase promoter to drive cell-directed expression of the desired gRNA.

First, a desired scaffold sequence is selected, which drives association between the guide RNA and the CRISPR enzyme. Such a scaffold sequence is generally a fusion of tracrRNA (~64 nt) and crRNA repeat sequence (~12 nt) joined by a loop sequence (4 nt), to which a targeting/protospacer sequence is attached to the 5' terminus.

A. Synthesis of Synthetic gRNAs

The structure of guide RNAs is uniquely amenable to solid-phase oligonucleotide synthesis, as the common domain (the scaffold/crRNA/tracrRNA/loop) is on the 3' terminus and the "variable" region (the protospacer domain/target region) is on the 5' terminus. Since solid-phase oligonucleotide synthesis proceeds 3' to 5', the guide RNA can be synthesized on the beads first, and then the pool of beads split into different reactions to synthesize the different protospacer domains. Additionally, the length of the gRNAs (~100 nt) is challenging to synthesize in high yield by traditional means; using a split procedure where the first and largest (~80 nt) part of the synthesis can be done in batch and scaled up as necessary makes it easier to ensure the final oligonucleotides are available in usable yield.

The gRNA scaffold is synthesized from 3' to 5' using 2'-O-thionocarbamate-protected adenine, uracil, cytosine, and guanine nucleoside phosphoramidites on a suitable solid support such as polystyrene resin using a single-column synthesizer such as the AKTA Oligo Pilot 100 plus or loading/washing using a fritted container (e.g. fritted filter funnel) and vacuum manifold on a nanomole to millimole scale. After coupling with the 5' most nucleotide phosphoramidite, the resin is capped using acetic anhydride/pyridine/THF 1/1/8 and 17.6% w/v N-methyl imidazole in acetonitrile. The resin is then washed with acetonitrile and flushed with argon.

The resin (now bound to the 3' terminus of the 80 nt gRNA scaffold) is split into 96 equal portions and loaded into each reaction vessel/channel of a 96 channel/vessel reaction plate of the multichannel synthesizer described above. The reaction plate is aligned with the registration features of the synthesizer and the clamp actuator seals the upper and lower face contacts of the reaction plate to the upper and lower manifolds of the synthesizer. The preloaded resin contained in the reaction vessels/channels of the reaction plate is swelled via flow of anhydrous acetonitrile from the wash system or the reagent delivery system. The remaining 17-20 nucleotides of the gRNA (the 5' most region/the protospacer domain/targeting sequence) are then coupled to the 5' of the gRNA scaffold attached to the resin by successive detritylation/deblocking (trichloroacetic acid in dichloromethane), chain elongation/coupling (phosphoramidite monomer/tetrazole in acetonitrile), capping (acetic anhydride/pyridine/THF and N-methylimidazole in acetonitrile), and oxidation (iodine in pyridine/THF) using 2'-O-thionocarbamate-protected A, C, U, and G nucleotide phosphoramidites. Using successive flows of A, C, U, and G phosphoramidites along with coupling reagents separated by acetonitrile during coupling cycles, the reagent control system is used to draw the phosphoramidite solution selectively into only the reaction vessels where that nucleotide is desired to be added.

After addition of the terminal (most 5') nucleotide of the protospacer domain, the resin is washed with acetonitrile and flushed with nitrogen, and then the reaction plate is removed from the synthesizer system. The reaction plate is placed in register with a 96-well deepwell or microwell polystyrene plate, and three resin volumes of concentrated aqueous ammonium hydroxide is added to the top frit of each channel/reaction vessel of the reaction plate to cleave the nucleotides from the resin. The plate is allowed to sit one hour at room temperature, and then the entire apparatus is placed in a centrifuge with a swinging bucket rotor and spun to elute the ammonium hydroxide solution into the deepwell/microwell plate. The deepwell/microwell plate containing the cleaved nucleotides is then frozen and placed in a lyophilizer to remove the ammonium hydroxide solution. The resultant lyophilized oligonucleotides are either desalted before use, or purified using reversed phase high-performance liquid chromatography (HPLC) before use.

B. Synthesis of DNAs Encoding gRNAs

Because at least one strand (antisense) of the DNAs encoding gRNAs are their reverse-complement, putting the variable region of the gDNAs (the protospacer domain) on the 3' terminus, this strand is synthesized via a one-step procedure in individual wells in the multichannel reaction plate of the multichannel synthesizer on polystyrene resin. The first 17-20 nucleotides of the protospacer domains (optionally preceded by nucleotides encoding a restriction enzyme cleavage site) are first synthesized in individual channels by successive detritylation/deblocking (trichloroacetic acid in dichloromethane), chain elongation/coupling (phosphoramidite monomer/tetrazole in acetonitrile), capping (acetic anhydride/pyridine/THF and N-methylimidazole in acetonitrile), and oxidation (iodine in water/pyridine/ THF) using A, C, T, and G traditional 2'deoxyribonucleotide phosphoramidites. Using successive flows of A, C, T, and G phosphoramidites separated by acetonitrile during coupling cycles, the reagent control system is used to draw the phosphoramidite solution selectively into only the reaction vessels where that nucleotide is desired to be added. After the protospacer domain, the nucleotides encoding the scaffold are added by simultaneous delivery to all the wells of the reaction plate (optionally followed by nucleotides encoding a restriction site either the same as or different to the optional restriction site added to the 3' terminus). After addition of the terminal (most 5') nucleotide of the scaffold or restriction site, the resin is washed with acetonitrile and flushed with nitrogen, and then the reaction plate is removed from the synthesizer system. The reaction plate is placed in register with a 96-well deepwell or microwell polystyrene plate, and greater than three resin volumes of concentrated aqueous ammonium hydroxide is added to the top frit of each channel/reaction vessel of the reaction plate to cleave the nucleotides from the resin. The plate is allowed to sit one hour at room temperature, and then the entire apparatus is placed in a centrifuge with a swinging bucket rotor and spun to elute the ammonium hydroxide solution into the deepwell/microwell plate. The deepwell/microwell plate containing the cleaved nucleotides is then frozen and placed in a lyophilizer to remove the ammonium hydroxide solution. The resultant lyophilized oligonucleotides are either desalted or purified using reversed phase high-performance liquid chromatography (HPLC).

Next, the sense strand (identical sequence) to the gRNA is synthesized using either the same procedure as the antisense strand, or using a two-step procedure similar to A above (except that A, C, T, and G deoxyribonucleotide phosphoramidites are used in place of 2'-O-thionocarbamate-protected A, C, U, and G nucleotide phosphoramidites). If used, the same restriction site sequences as the antisense strand are added to the synthetic nucleotide. The resultant lyophilized oligonucleotides are either desalted or purified using reversed phase high-performance liquid chromatography (HPLC).

Finally, both nucleotides for each gRNA sequence are combined in equal amounts (e.g. in a multiwell PCR plate) in a suitable aqueous buffer (e.g. Tris pH 8.0), the strands are denatured by heating at 95 degrees Celsius, and annealed by slow cooling to room temperature.

Example 2

Multi-Column Synthesis of 96-Member 20-Mer Target Peptide Library with Identical Cell Penetrating Peptide Sequence As not all synthetic peptides composed of natural amino acids have high cell permeability, a common approach in development of therapeutic peptides is the addition of a cell-penetrating peptide sequence (e.g. penetratin, TAT peptide, pVEC, transportan, MPG, Pep-1, MAP, $R_6W_3$) to the N- or C-terminus of the desired therapeutic sequence to improve access of the sequence to intracellular proteins (e.g. for protein-protein interaction inhibition or enzyme inhibition). The addition of additional peptide sequences to the therapeutic peptides complicates synthesis, as the addition of more amino acids lowers the overall yield of the peptide synthesis. Assuming a 20 amino acid therapeutic peptide and 80% yield of each coupling step, attaching penetratin (RQIKIWFQNRRMKWKK (SEQ ID NO: 1)), for example, lowers the theoretical yield of the complete peptide from $(0.8)^{20} \times 100=1.15\%$ to $(0.8)^{36} \times 100=0.03\%$. Using the methods and systems described herein, combinatorial libraries of peptides comprising different therapeutic/targeting moieties (e.g. 96 different targeting moieties) and the same cell penetrating peptide (e.g. penetratin) can be synthesized in a single batch via a two-phase process. In this process, the cell penetrating peptide (RQIKIWFQNRRMKWKK (SEQ ID NO: 1), for example) is first synthesized attached to beads, and then the pool is split to further synthesize the individual targeting/therapeutic moieties from the nascent cell-penetrating peptide.

First, the cell-penetrating peptide RQIKIWFQN-RRMKWKK (SEQ ID NO: 1) is synthesized from C- to N-terminus using Fmoc protected amino acids and standard coupling conditions using HBTU/N,N-diisopropylethylamine (see e.g. Coin et al. Nat Protoc. 2007; 2(12):3247-56) on a suitable solid support such as polystyrene resin (e.g. Wang resin or resin preloaded with Fmoc-L-Arg) using a single-column synthesizer or loading/washing using a fritted container (e.g. fritted filter funnel) and vacuum manifold on a nanomole to millimole scale. After coupling with the N-terminal most Fmoc-protected amino acid (in this case, Lysine), the resin is washed with solvent (e.g. DMF, DCM, or both) and dried under air or inert gas.

Next, the resin (now bound to the C-terminus of the cell-penetrating peptide RQIKIWFQNRRMKWKK (SEQ ID NO: 1)) is split into 96 equal portions and loaded into each reaction vessel/channel of a 96 channel/vessel reaction plate of the multichannel synthesizer described above. The reaction plate is aligned with the registration features of the synthesizer and the clamp actuator seals the upper and lower face contacts of the reaction plate to the upper and lower manifolds of the synthesizer. The preloaded resin contained in the reaction vessels/channels of the reaction plate is swelled via flow of anhydrous DMF from the wash system or the reagent delivery system. The remaining 20 amino acids of the peptide (the N-terminal most region/the "targeting" sequence) are then coupled to the N-terminus of the cell-penetrating peptide attached to the resin by successive deprotection (piperidine in DMF), chain elongation/coupling (Fmoc-protected amino acid with HBTU and DIEA in DMF), and washing (DMF) using Fmoc-protected amino acids. Using successive flows of each of the Fmoc-amino acids desired at each position along with coupling reagents through the lower manifold during coupling cycles, the reagent control system is used to draw the activated Fmoc-amino acid solution into only the reaction vessels where that amino acid is desired to be added.

After addition of the terminal (most N-terminal) amino acid of the "targeting" portion of the peptide, the N-terminal Fmoc group is removed using piperidine in DMF, the resin is washed with DMF and/or DCM, and the resin is flushed with inert gas/argon to dry. The reaction plate is then removed from the synthesizer system. The reaction plate is sealed on the bottom and greater than three resin volumes of cleavage solution (e.g. TFA/H$_2$O/phenol/TIPS 8.5/0.5/0.5/0.5) is added to each channel/reaction vessel of the reaction plate. The reaction plate is agitated and allowed to sit 3 hours at room temperature, after which the bottom seal is removed, the plate is placed in register with a 96-well polypropylene or polystyrene microwell/deepwell plate containing cold ether, and the cleavage solution is eluted (e.g. via centrifugation) into each well of the 96-well polypropylene or polystyrene microwell/deepwell plate to precipitate the peptide. Centrifugation and decanting is then used to isolate the precipitated peptide, which is washed with ether and dried overnight, after which each of the 96 peptides can be purified by reversed phase high-performance liquid chromatography (HPLC).

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. Although the synthesis system described is directed to the production of DNA and RNA, the system and method may be readily adapted by substitution or addition of various reagents to the synthesis of a wide range of biopolymers where it is necessary or desirable to synthesize a large number of different compounds in an automated and efficient manner. It is intended that the following claims define the scope of the invention and that methods and structures within the scope of these claims and their equivalents be covered thereby.

What is claimed is:

1. A method of synthesizing a plurality of single molecule guide RNAs (sgRNAs) comprising identical scaffold sequences and multiple different protospacer domains targeting distinct genomic regions, the method comprising:

(a) synthesizing a plurality of identical scaffold sequences onto a plurality of solid supports in a single vessel of a first oligosynthesizer;

wherein each of the plurality of identical scaffold sequences consists of a fusion of a transactivating clustered regularly interspaced palindromic repeat RNA (tracrRNA) sequence and a clustered regularly interspaced palindromic repeat RNA (crRNA) repeat sequence joined by a loop sequence to form a plurality of identical scaffold sequences, such that each of the plurality of solid supports comprises one or more of the plurality of identical scaffold sequences covalently bound to the 3' end of the tracrRNA sequence;

(b) splitting the plurality of solid supports into a plurality of separate reaction vessels; and (c) coupling, in a different oligonucleotide synthesizer, a plurality of different protospacer domains to the 5' end of the plurality of identical scaffold sequences bound to the plurality of solid supports within each of the plurality of separate reaction vessels to synthesize a plurality of different single guide RNAs (sgRNAs), such that after the coupling each separate reaction vessel comprises a plurality of identical sgRNAs, wherein each of the plurality of different protospacer domains is specific to a DNA target site, and wherein the coupling of each of the plurality of different protospacer domains comprises phosphoramidite coupling of nucleotide monomers starting from the 5' end of each of the plurality of identical scaffold sequences and/or phosphoramidite coupling of different oligonucleotides; and (d) cleaving the plurality of synthesized sgRNAs from the plurality of identical scaffold sequences, wherein each of the plurality of synthesized sgRNAs is ~100 nucleotides (nt) in length.

2. The method of claim 1, wherein the plurality of solid supports comprise a polystyrene resin.

3. The method of claim 1, wherein the nucleotide monomers are selected from the group consisting of an adenine deoxyribonucleoside phosphoramidite, a thymine deoxyribonucleoside phosphoramidite, a cytosine deoxyribonucleoside phosphoramidite, a guanine deoxyribonucleoside phosphoramidite, and a combination thereof.

4. The method of claim 1, wherein the each of the plurality of identical scaffold sequences comprises an RNA polynucleotide about 80 nucleotides in length.

5. The method of claim 1, wherein each of the plurality of different protospacer domains of the sgRNAs is about 17 to 22 nucleotides in length.

6. The method of claim 1, further comprising adding ammonium hydroxide to the plurality of separate reaction vessels to cleave one or more of the plurality of synthesized sgRNAs from the solid support.

7. The method of claim 6, further comprising lyophilizing the plurality of synthesized sgRNAs.

8. The method of claim 7, further comprising desalting the plurality of synthesized sgRNAs.

9. The method of claim 7, wherein purifying the plurality of synthesized sgRNAs comprises reverse phase high performance liquid chromatography.

10. The method of claim 9, wherein purifying the plurality of synthesized sgRNAs comprises reverse phase high performance liquid chromatography.

11. The method of claim 1, further comprising: acquiring a sample of the plurality of solid supports from the first oligosynthesizer after step (a) and before splitting the plurality of solid supports into the plurality of separate reaction vessels in step (b), assessing a quantity of the plurality of identical scaffold sequences bound to the plurality of solid supports within the acquired sample; and prior to step (c), determining the quantity of the plurality of identical scaffold sequences synthesized in the first oligosynthesizer within the single vessel based on an assessed quantity of the plurality of identical scaffold sequences in the acquired sample.

12. The method of claim 11, further comprising: determining the quantity of the plurality of solid supports to be split into the plurality of separate reaction vessels in step (b) based on an assessed quantity of the plurality of identical scaffold sequences within the acquired sample.

13. The method of claim 12, further comprising: cleaving the plurality of identical scaffold sequences from the plurality of solid supports within the sample before assessing the quantity of the plurality of identical scaffold sequences within the acquired sample.

14. The method of claim 1, wherein the nucleotide monomers are selected from the group consisting of a 2'-O-thionocarbamate protected adenine nucleoside phosphoramidite, a 2'-O-thionocarbamate-protected uracil nucleoside phosphoramidite, a 2'-O-thionocarbamate-protected cytosine nucleoside phosphoramidite, a 2'-O-thionocarbamate-protected guanine nucleoside phosphoramidite, and a combination thereof.

15. The method of claim 1, wherein each of the plurality of separate reaction vessels comprises a different protospacer domain.

* * * * *